(12) United States Patent
Yokoi et al.

(10) Patent No.: US 7,637,864 B2
(45) Date of Patent: Dec. 29, 2009

(54) MEDICAL DEVICE

(75) Inventors: Takeshi Yokoi, Hino (JP); Hironobu Takizawa, Hachioji (JP); Akio Uchiyama, Saitama (JP); Kenichi Arai, Shiogama (JP); Kazushi Ishiyama, Sendai (JP); Masahiko Sendou, Sendai (JP)

(73) Assignee: Olympus Corporation, Tokyo (JP)

( * ) Notice: Subject to any disclaimer, the term of this patent is extended or adjusted under 35 U.S.C. 154(b) by 726 days.

(21) Appl. No.: 10/541,369

(22) PCT Filed: Dec. 5, 2003

(86) PCT No.: PCT/JP03/15584

§ 371 (c)(1),
(2), (4) Date: Jul. 5, 2005

(87) PCT Pub. No.: WO2004/066830

PCT Pub. Date: Aug. 12, 2004

(65) Prior Publication Data

US 2006/0169293 A1   Aug. 3, 2006

(30) Foreign Application Priority Data

Jan. 30, 2003   (JP) .............................. 2003-022708

(51) Int. Cl.
*A61B 1/00* (2006.01)
(52) U.S. Cl. .................. 600/114; 600/118
(58) Field of Classification Search ............. 600/101, 600/114, 117, 118, 127, 421–424, 434; 606/80, 606/170, 171, 180; 607/143; 408/210, 224, 408/230
See application file for complete search history.

(56) References Cited

U.S. PATENT DOCUMENTS

| | | | |
|---|---|---|---|
| 3,821,956 A | 7/1974 | Gordhamer | |
| 4,176,662 A * | 12/1979 | Frazer | ......................... 600/114 |
| 5,102,414 A | 4/1992 | Kirsch | |
| 5,318,557 A | 6/1994 | Gross | |
| 5,353,807 A | 10/1994 | DeMarco | |
| 5,551,443 A * | 9/1996 | Sepetka et al. | ............... 600/585 |
| 5,681,260 A | 10/1997 | Ueda et al. | |
| 5,954,714 A * | 9/1999 | Saadat et al. | ................... 606/28 |
| 5,989,230 A | 11/1999 | Frassica | |
| 6,007,481 A * | 12/1999 | Riek et al. | .................... 600/114 |
| 6,224,608 B1 * | 5/2001 | Ciccolella et al. | ........... 606/108 |
| 6,503,251 B1 | 1/2003 | Shadduck | |
| 6,814,734 B2 * | 11/2004 | Chappuis et al. | ............... 606/80 |

(Continued)

FOREIGN PATENT DOCUMENTS

CN   2364843 Y   2/2000

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A capsule medical apparatus inserted in the body cavity includes a spiral projected portion on the outer peripheral surface of a body cavity inserting portion. The pitch, height, and cross section of the projected portion and the like are set to have proper values and shapes suitable to the advance thereof. The body cavity inserting portion has a magnet. An external magnetic guiding device applies a rotating magnetic field to the magnet and the magnetic torque acts on a magnet for rotation. Thus, the medical apparatus stably advances.

20 Claims, 22 Drawing Sheets

U.S. PATENT DOCUMENTS

| | | | |
|---|---|---|---|
| 7,445,596 B2* | 11/2008 | Kucklick et al. | 600/114 |
| 2003/0009222 A1* | 1/2003 | Fruh et al. | 623/17.11 |
| 2003/0020810 A1* | 1/2003 | Takizawa et al. | 348/68 |
| 2003/0060734 A1* | 3/2003 | Yokoi et al. | 600/593 |
| 2003/0065361 A1* | 4/2003 | Dreyfuss | 606/232 |
| 2003/0167000 A1* | 9/2003 | Mullick et al. | 600/424 |
| 2003/0181788 A1* | 9/2003 | Yokoi et al. | 600/160 |
| 2003/0229268 A1* | 12/2003 | Uchiyama et al. | 600/109 |
| 2005/0031665 A1* | 2/2005 | Watson et al. | 424/423 |
| 2005/0143644 A1* | 6/2005 | Gilad et al. | 600/407 |

FOREIGN PATENT DOCUMENTS

| | | |
|---|---|---|
| EP | 0 651 667 B1 | 5/1995 |
| GB | 255533 | 7/1926 |
| JP | 06-063045 | 3/1994 |
| JP | 8-503384 | 4/1996 |
| JP | 8-216876 | 8/1996 |
| JP | 3017770 | 12/1999 |
| JP | 2001-104243 | 4/2001 |
| JP | 2001-179700 | 7/2001 |
| JP | 2002-187100 | 7/2002 |
| WO | WO 94/01165 | 1/1994 |

* cited by examiner

OUTLINE OF THE EXAMINATION

CONVERT ROTATION INTO THRUST WITH SPIRAL STRUCTURE
EXAMINE SPIRAL-SHAPE INFLUENCE ON CAPSULE DRIVING CHARACTERISTIC
· ADVANCING VELOCITY
· LOAD TORQUE

1ST EXPERIMENT -MEASUREMENT OF ADVANCING VELOCITY-

SPIRAL SHAPE USED FOR EXAMINATION a: SPIRAL PITCH (5, 10, 15 mm)
b: SPIRAL HEIGHT (1.5, 3, 4.5 mm)
c: SPIRAL CROSS-SECTION
d: SPIRAL EDGE SHAPE
e: NUMBER OF SPIRAL

DIAMETER: 11 mm, LENGTH: 40 mm

EXPERIMENT RESULT SPIRAL PITCH

FIG. 10
EXPERIMENT RESULT SPIRAL HEIGHT
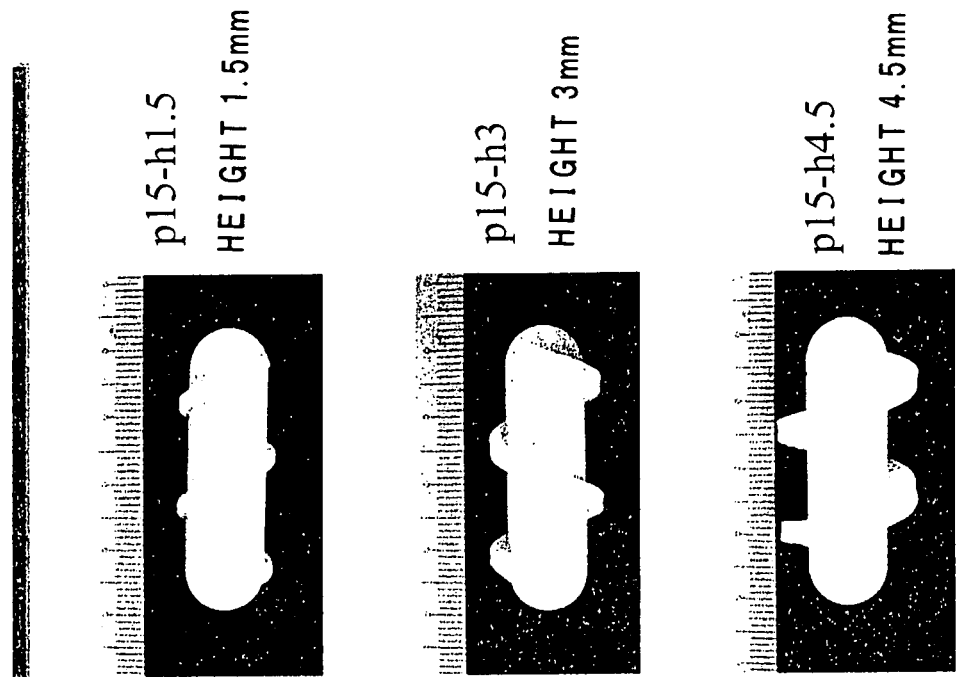
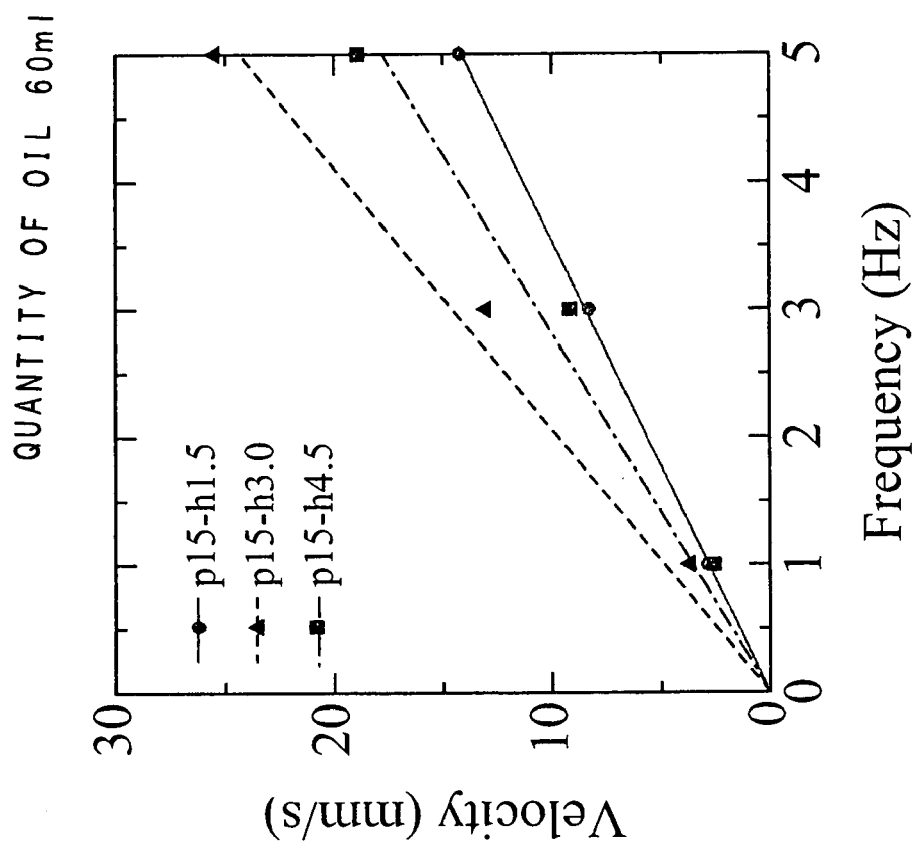

FIG.11
EXPERIMENT RESULT SPIRAL HEIGHT
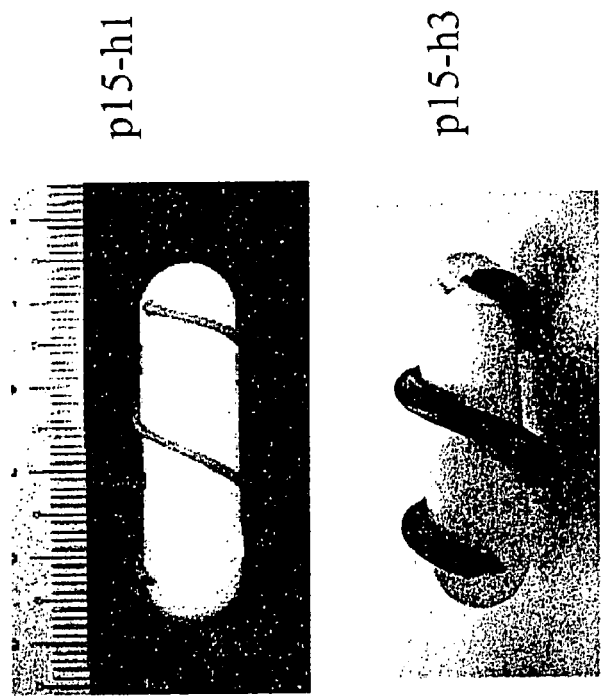
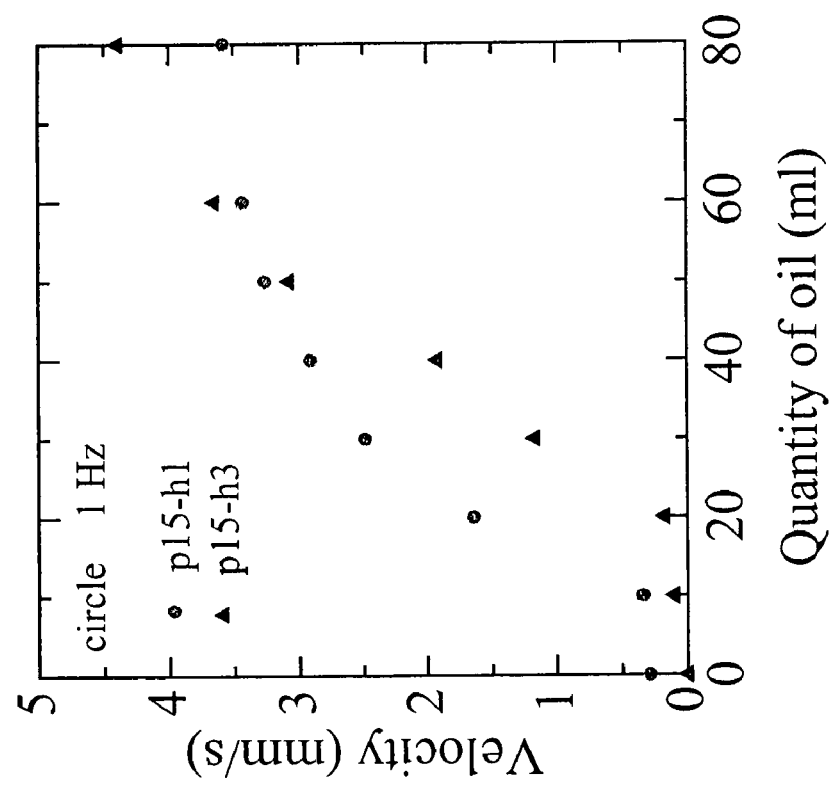

EXPERIMENT RESULT   SPIRAL CROSS-SECTION

EXPERIMENT RESULT   SPIRAL EDGE SHAPE

FIG. 14
EXPERIMENT RESULT NUMBER OF SPIRAL
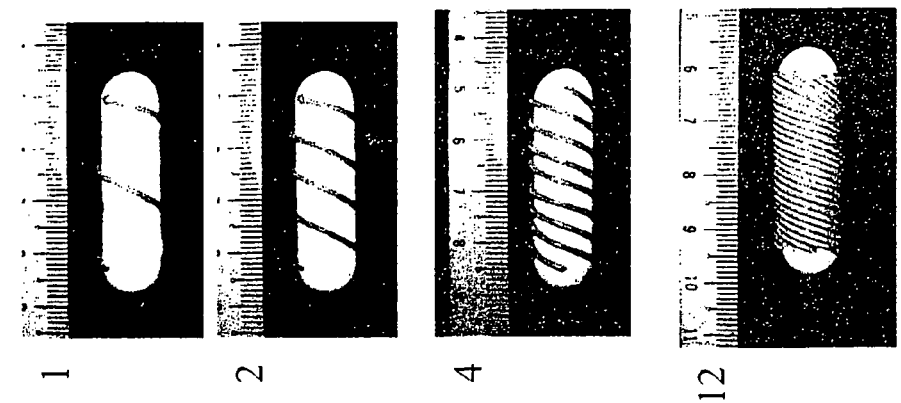
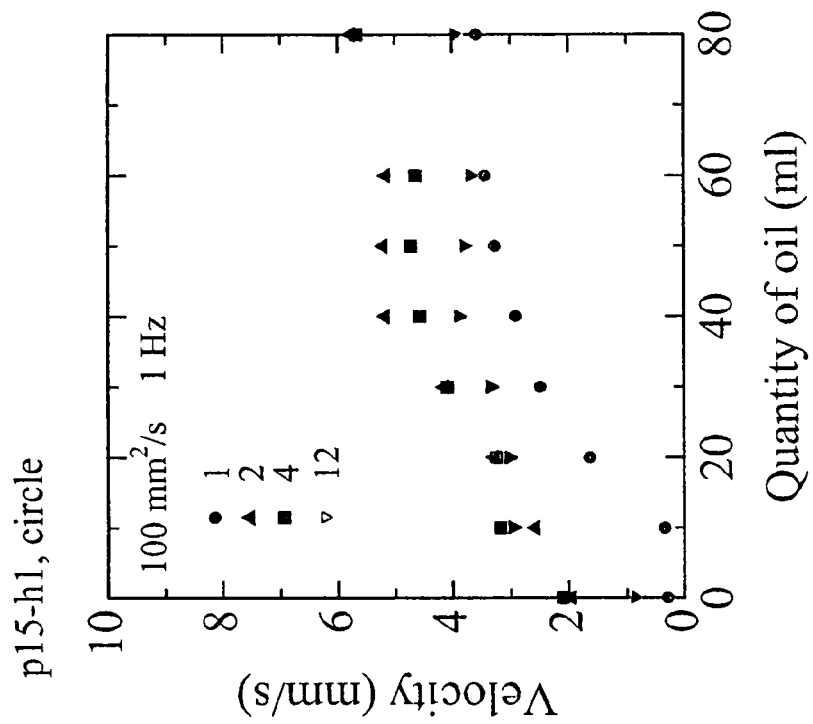

| NUMBER OF TIMES OF ROTATING DEFECT | | | | SPIRAL SHAPE | |
|---|---|---|---|---|---|
| TYPE | 1Hz | 3Hz | 5Hz | SPIRAL HEIGHT | SPIRAL PITCH |
| a | 0 | 0 | 0 | 1.5 mm | 5 mm |
| b | 0 | 0 | 0 | 1.5 mm | 10 mm |
| c | 0 | 0 | 0 | 1.5 mm | 15 mm |
| d | 0 | 0 | 1 | 3 mm | 5 mm |
| e | 0 | 0 | 3 | 3 mm | 10 mm |
| f | 0 | 1 | 2 | 3 mm | 15 mm |
| g | 0 | 3 | 5 | 4.5 mm | 5 mm |
| h | 0 | 4 | 5 | 4.5 mm | 10 mm |
| i | 0 | 4 | 5 | 4.5 mm | 15 mm |

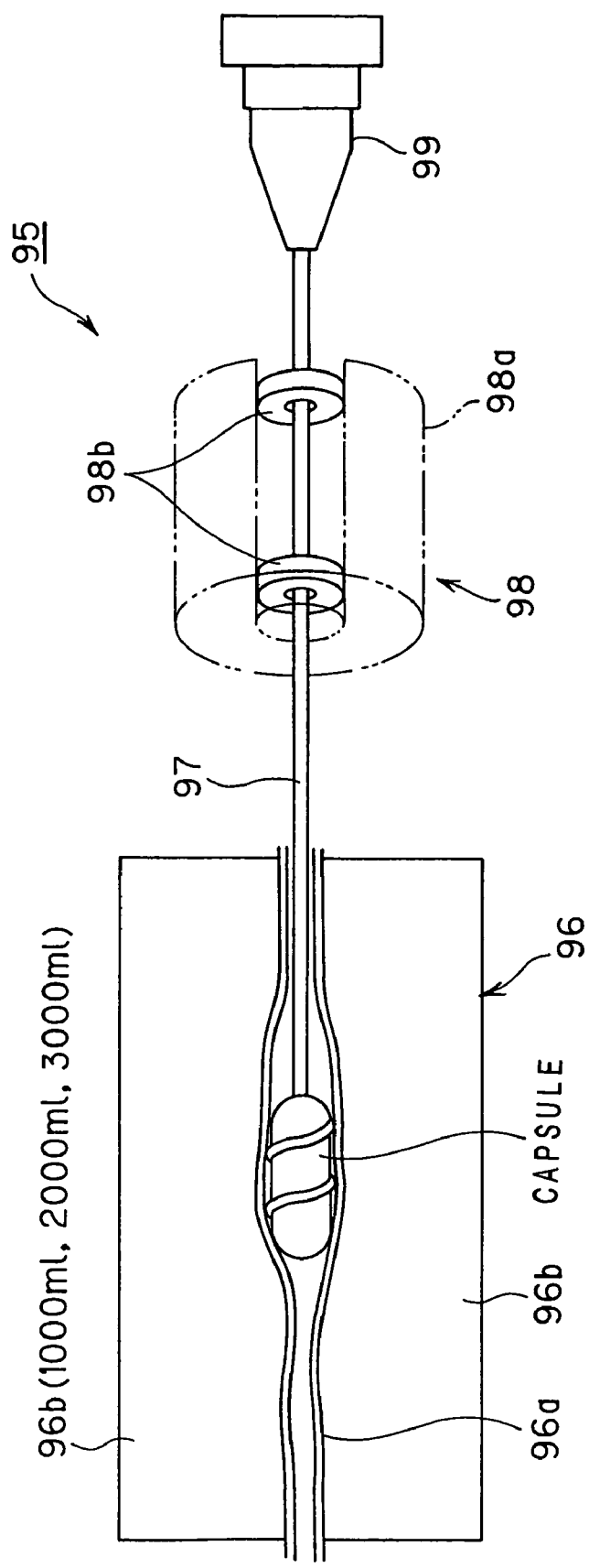

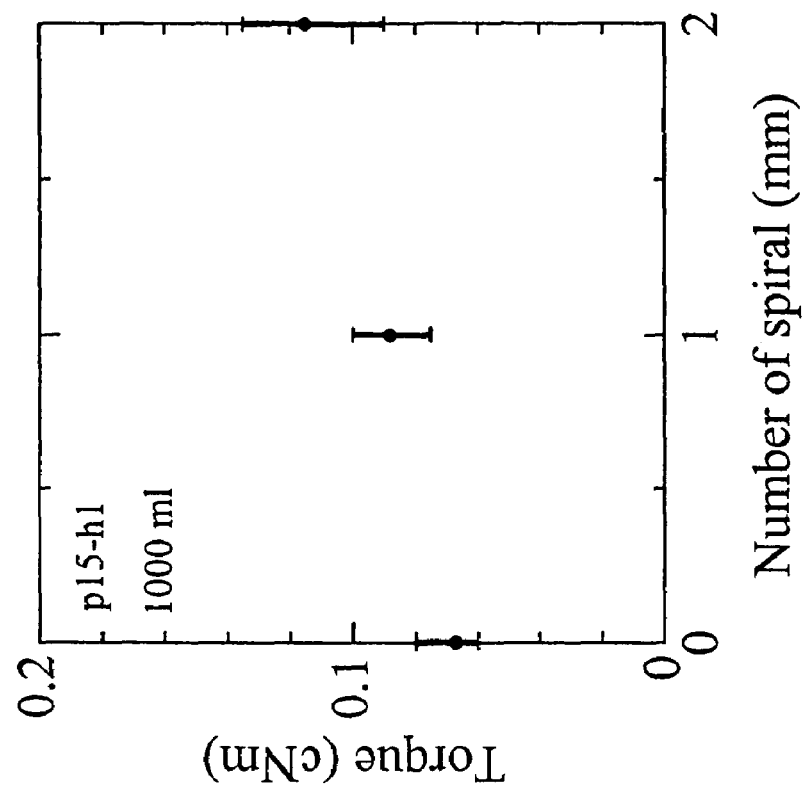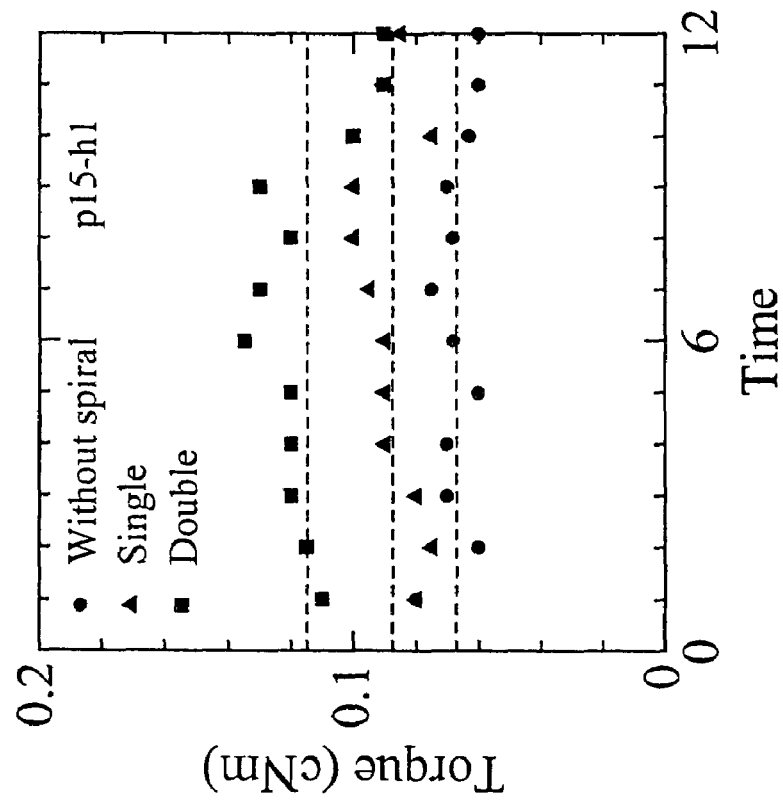
FIG. 18A
FIG. 18B

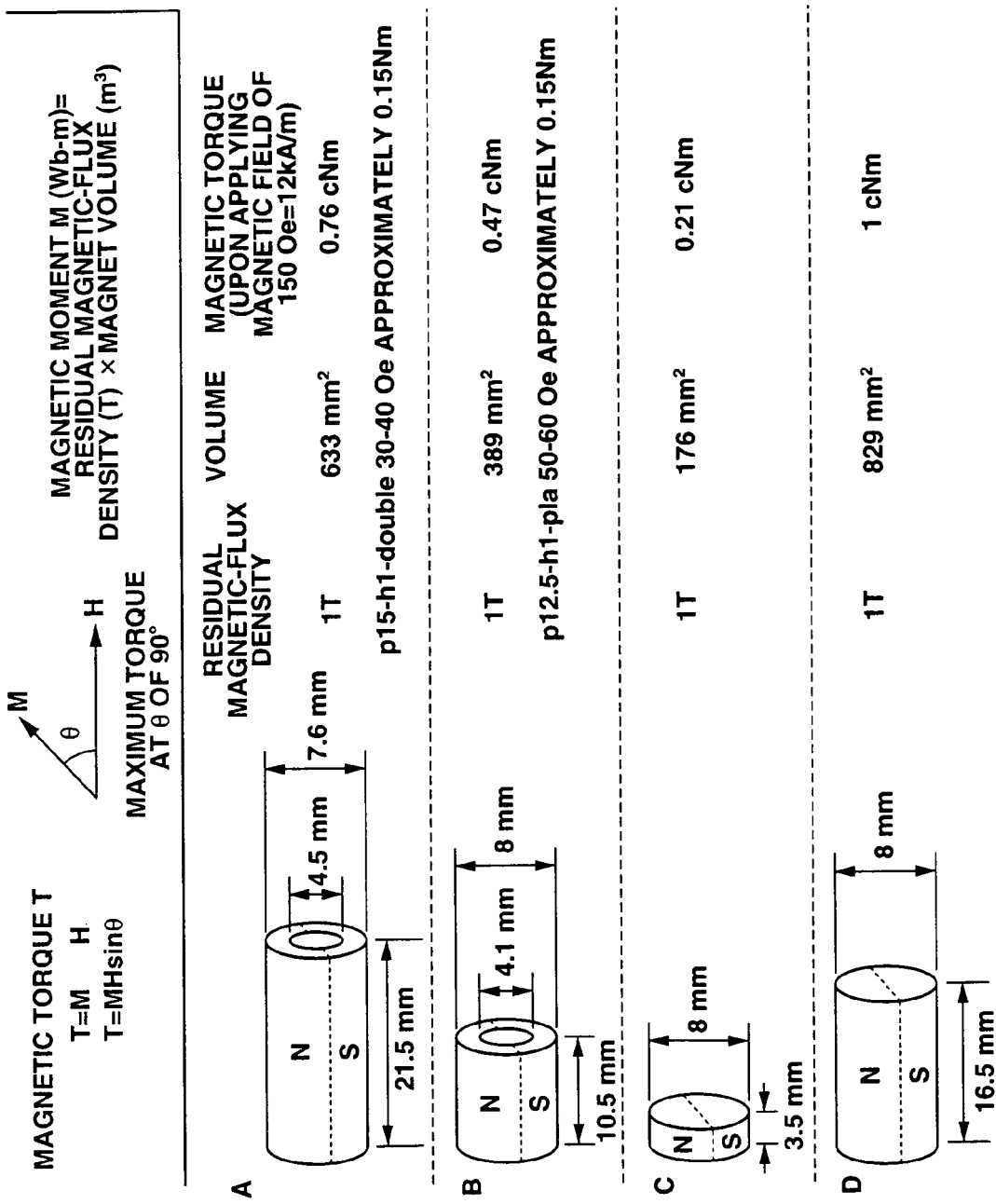

FIG.21A
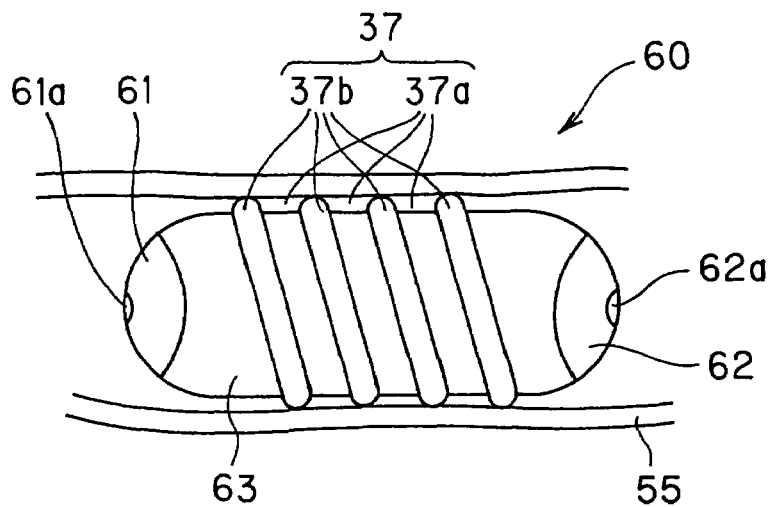
FIG.21B
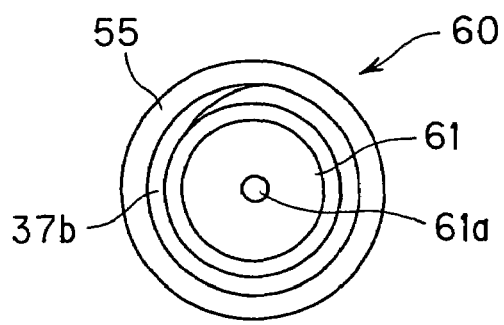
FIG.22A  FIG.22B  FIG.22C
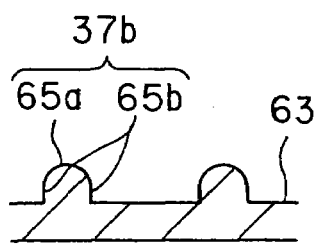 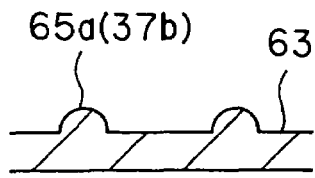 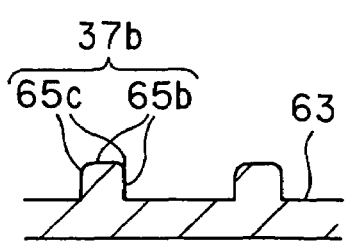
FIG.22D
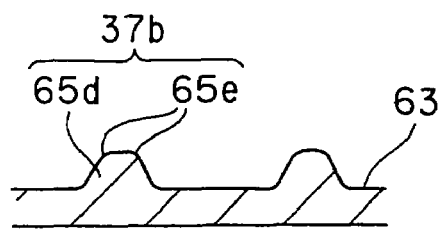

MEDICAL DEVICE

TECHNICAL FIELD

The present invention relates to a medical apparatus which rotates and advances in the body cavity by a rotating magnetic field or the like.

BACKGROUND ART

Japanese Patent No. 3017770 discloses a medical apparatus as a first conventional art for magnetically guiding in a sample.

According to the first conventional art, the medical apparatus comprises a guided portion which is magnetically guided at least to a part of an inserting portion inserted in the sample, and moving means which moves magnetic force generating means arranged out of the sample in the direction that balances in the one guided direction and in the direction that cannot control the balance.

Further, Japanese Patent No. 3017770 discloses a method for magnetically guiding a general endoscope inserting portion or a capsule endoscope. Furthermore, Japanese Patent No. 3017770 discloses a method for vibrating the endoscope inserting portion by an AC magnetic field and rotating and guiding the capsule endoscope.

Japanese Unexamined Patent Application Publication No. 2001-179700 discloses a medical apparatus which comprises a magnetic field generating unit which generates a rotating magnetic field, and a robot main body which receives the rotating magnetic field and obtains the thrust, wherein the surface of the rotating magnetic field can be changed in a predetermined direction in the three-dimensional space.

As disclosed in Japanese Unexamined Patent Application Publication No. 2001-179700, as a thrust generating unit, mechanical means such as a spiral or a screw suitable to the advance in the fluid is arranged to the robot main body and a drill unit is arranged to the front end and rear end of the robot main body so as to be movable if a solid material or gel material exists in the advance direction.

However, the first conventional art has the following problems.

That is, the magnetic force generating means out of the sample must be moved in accordance with the direction for guiding the guided portion. Therefore, the moving means arranged outside the body has the complicated structure and the control operation. Hence, the body cavity inserting portion does not stably advance in the body cavity.

Further, the capsule endoscope does not have the thrust generating unit for converting rotating force into the thrust on the outer surface. Therefore, the lost motion is caused in the body cavity in many cases and the stable thrust is not obtained.

Moreover, according to the second conventional art, the body cavity inserting portion in the medical apparatus receives the rotating magnetic field and the stable advance in contact with the inner wall in the body cavity are not considered. Therefore, if the disclosed contents are directly applied, the following problems are caused.

(a) The shape of the thrust generating unit (spiral, screw, or drill) is not optimal and therefore the lost motion is caused in a non-contact state with the inner wall in the body cavity. If the contact state is realized, the thrust speed is slow per rotation.

(b) The optimal magnetic torque is not considered and therefore the torque is not sufficiently obtained, or the magnetic torque more than necessary is obtained but an extra-body device is increased in size.

Therefore, the present invention is devised in consideration of the problems of the first and second conventional arts and it is one object of the present invention to provide a medical apparatus, in which the body cavity inserting portion stably advances in contact with the inner wall in the body cavity by receiving the rotating magnetic field.

It is another object of the present invention to provide a medical apparatus having the thrust generating unit which is optimal for the body cavity inserting portion to stably advance in the body cavity.

It is another object of the present invention to provide a medical apparatus, in which it is possible to generate and arbitrarily set the magnetic torque that is optimal for the body cavity inserting portion to stably advance in the body cavity.

DISCLOSURE OF INVENTION

According to the present invention, there is provided a medical apparatus inserted in a body cavity, comprising a body cavity inserting portion having a projected portion that is spiral-shaped for generating thrust in contact with the body cavity, wherein the projected portion has the structure which satisfies at least one of five conditions including the pitch of 10 mm or more, the height of 0.3 mm or more and 3 mm or less, the cross-sectional shape that is substantially semi-circular or substantially trapezoidal, the inclining angle of an end portion of 45° or less, and the number of spirals that is 2 or more and 10 or less.

BRIEF DESCRIPTION OF THE DRAWINGS

FIG. 1 to FIG. 23B relate to a first embodiment of the present invention, FIG. 1 is a diagram showing the entire structure of a medical system according to the first embodiment of the present invention;

FIG. 2 is a block diagram showing the structure of an electric system in a capsule medical apparatus;

FIG. 3A is a longitudinal cross-sectional view of the capsule medical apparatus, FIG. 3B is a front view from the front end side in FIG. 3A, FIG. 3C is a rear view from the rear end side in FIG. 3A, and FIG. 3D is a longitudinal cross-sectional view of the capsule medical apparatus having a two-spiral projected portion;

FIG. 4 is a diagram showing a driving principle for advancing a capsule having a magnet by applying a rotating magnetic field to the capsule;

FIG. 6 is a schematic diagram showing the items examined in the capsule medical apparatus according to the first embodiment;

FIG. 7 is a diagram showing the structure of a device used for measurement of an advancing velocity;

FIG. 8 is a schematic diagram showing the items examined about the spiral shape of the capsule medical apparatus according to the first embodiment;

FIG. 9 is a diagram showing measurement data upon changing a spiral pitch;

FIG. 10 is a diagram showing the measurement data upon changing a spiral height;

FIG. 11 is a diagram showing the measurement data upon changing the quantity of oil, depending on different spiral heights;

FIG. 12 is a diagram showing the measurement data, depending on different spiral cross-sections;

FIG. 13 is a diagram showing the measurement data, depending on different spiral end portion shapes;

FIG. 14 is a diagram showing the measurement data, depending on the different numbers of spiral;

FIG. 16 is a diagram showing the schematic structure of a torque measuring device;

FIGS. 18A and 18B are diagrams showing the measurement data of torque which is required for rotation, depending on the presence or absence of the spiral and the different number of spiral;

FIG. 20 is a diagram showing the magnet size and a value or the like of a magnetic torque upon applying a predetermined external magnetic field;

FIGS. 21A and 21B show the structure of a capsule medical apparatus having a treatment tool storage portion and an ultrasonic portion according to a first modification, FIG. 21A is a side view showing the capsule medical apparatus in the using state in the small intestine, FIG. 21B is a front view showing the capsule medical apparatus from the front side;

FIGS. 22A to 22D are diagrams showing the specific shapes of an R shape in a spiral projected portion;

FIGS. 23A and 23B are diagrams showing the structure of a capsule medical apparatus according to a second modification, FIG. 23A is a diagram showing a state of using, in the small intestine or the like, the capsule medical apparatus in which an elastic rubber cover is detachably attached to a capsule main body, and FIG. 23B is a perspective view showing the elastic rubber cover;

FIG. 24 is a diagram showing the structure of a capsule medical apparatus according to the second embodiment;

FIG. 25 is a cross-sectional view schematically showing the structure of a rotatable portion in FIG. 24;

FIG. 26 is a diagram showing a part according to a first modification; and

FIG. 27 is a cross-sectional view enlarging and showing the structure around a projected portion according to a second modification.

BEST MODE FOR CARRYING OUT THE INVENTION

Hereinbelow, embodiments of the present invention are described with reference to the drawings.

FIRST EMBODIMENT

The first embodiment of the present invention will be described with reference to FIGS. 1 to 23B.

Figure 1:
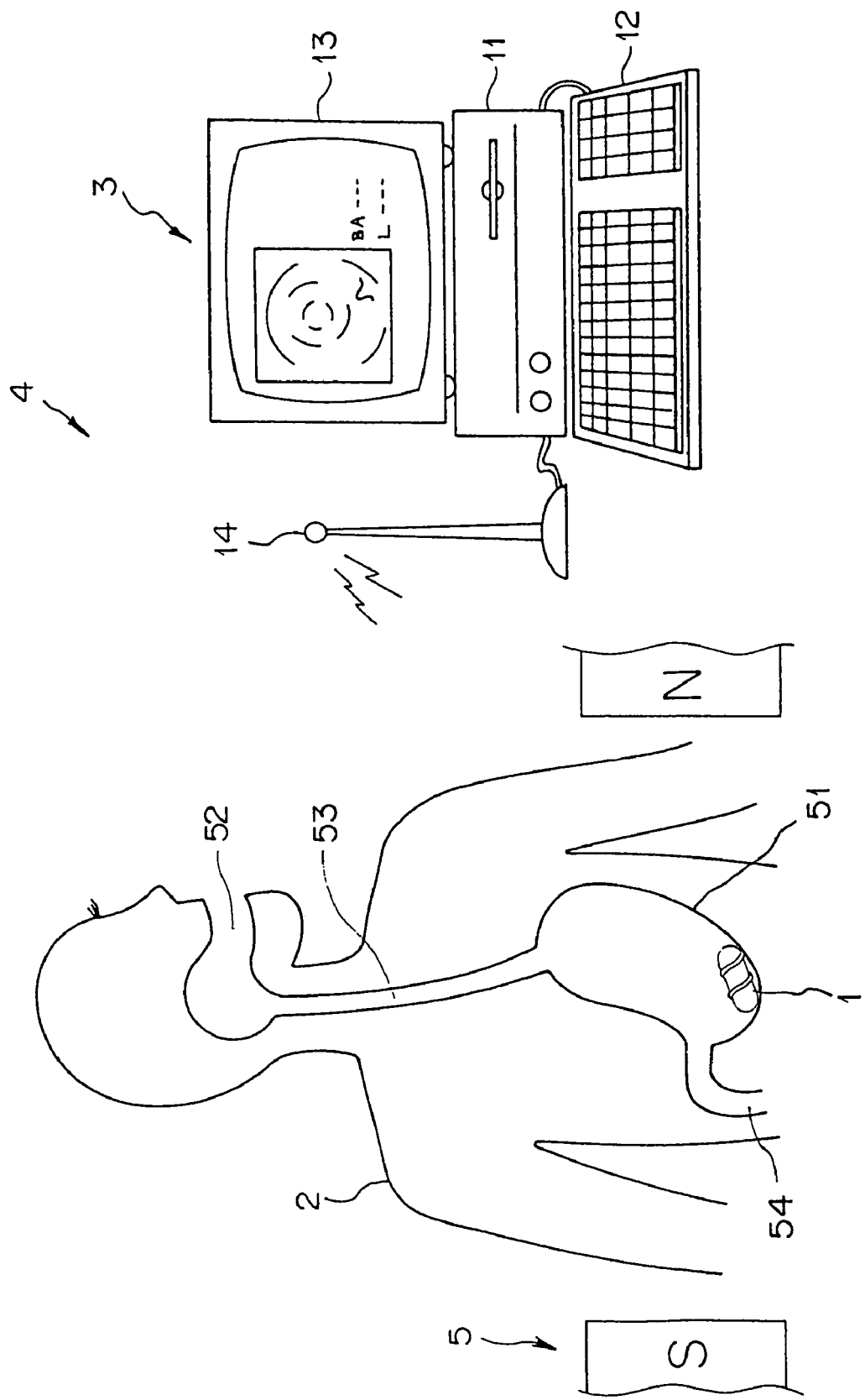
Figure 2:
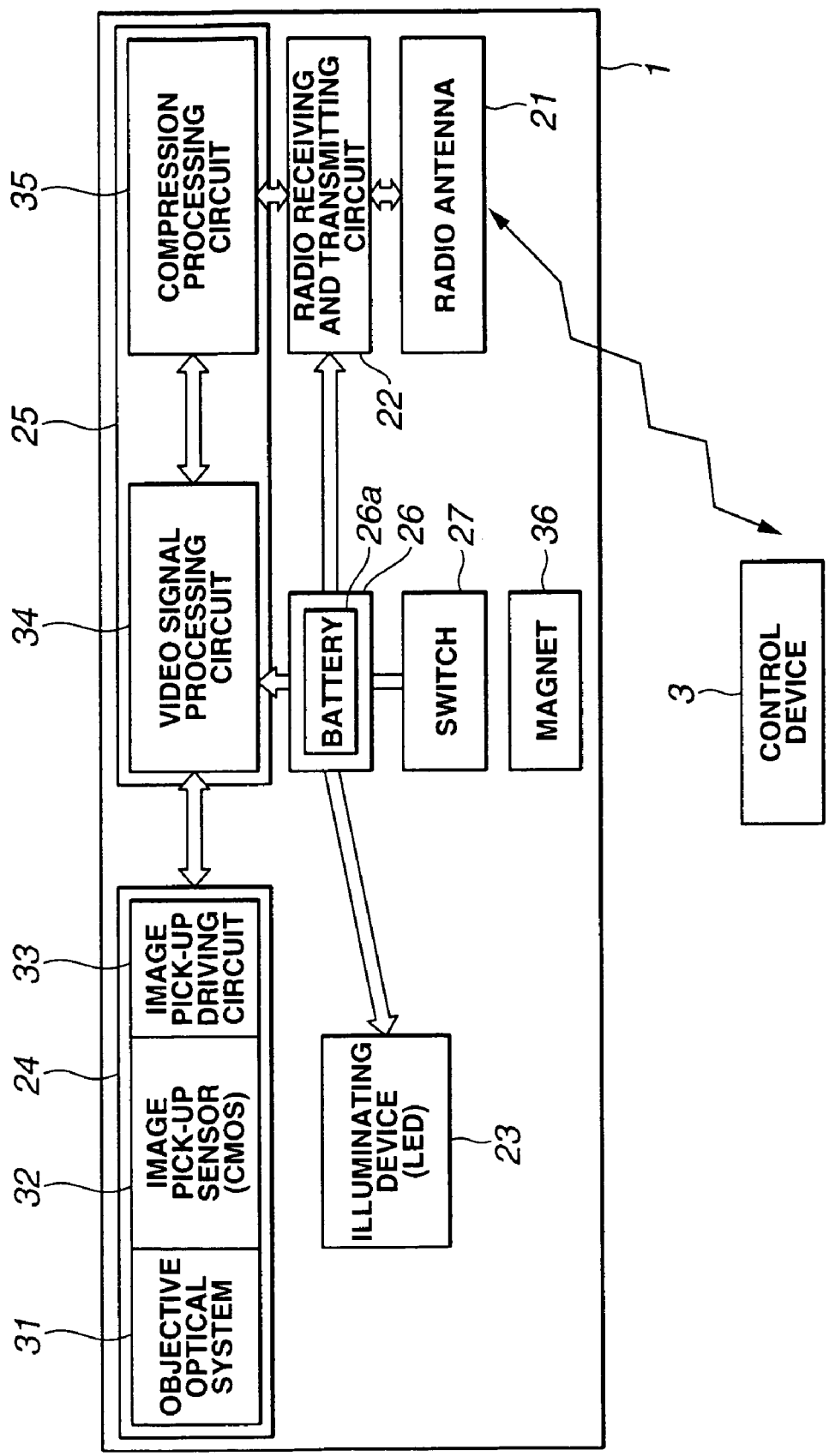

Referring to FIG. 1, a capsule medical apparatus 1 having a body cavity inserting portion which is inserted in the body cavity forms a medical system 4 which receives electric waves from/to a capsule control device (hereinafter, referred to as a control device) 3 arranged outside the body during the passage of the luminal portion in the body cavity of a patient 2 and thus can perform medical actions such as examination, curing, and treatment under the control of the control device 3.

The medical system 4 has a magnetic guiding device 5, as magnetic field generating means, which generates a rotating magnetic field around the patient 2. The magnetic guiding device 5 smoothly advances the capsule medical apparatus 1 having the body cavity inserting portion in the body cavity of the patient 2. In FIG. 1, the magnetic guiding device 5 is schematically shown.

The medical system 4 is swallowed together with water, similar to a medicine and performs the screening examination of the esophagus, the duodenum, the small intestine, and the large intestine, after the pre-processing for the large intestine (cleaning the intestinal canal). When the capsule medical apparatus 1 passes through the esophagus fast, it picks up an image every 10 frames per second. When the capsule medical apparatus 1 passes through the small intestine slowly, it picks up the image every 2 frames per second. The picked-up image is subjected to the necessary signal processing and digital compression processing, then, the image is transferred to the control device 3, and it is recorded so as to execute the diagnosis referring to only essential information as a moving image.

The magnetic guiding device 5 forms the rotating magnetic field for magnetically acting to a magnet 36, which will be described later. The magnet 36 is arranged in a capsule main body 6 forming the capsule medical apparatus 1. Further, the magnetic guiding device 5 is connected to the control device 3 so as to control the direction of the generated rotating magnetic field.

The control device 3 comprises: a PC main body 11 having a function for controlling the capsule medical apparatus 1 and the magnetic guiding device 5; a keyboard 12 which is connected to the PC main body 11 and inputs a command and data and the like; a monitor 13, as display means, which is connected to the PC main body 11 and displays the image; and an extra-body antenna 14 which is connected to the PC main body 11 and transmits a control signal for controlling the capsule medical apparatus 1 and receives the signal from the capsule medical apparatus 1.

The control device 3 generates the control signal for controlling the capsule medical apparatus 1 and the magnetic guiding device 5 based on a key input from the keyboard 12 or a control program which is stored in a hard disk or the like in the PC main body 11.

The generated control signal for controlling the magnetic guiding device 5 is transmitted to the magnetic guiding device 5 via a connecting cable (not shown) from the PC main body 11.

The magnetic guiding device 5 forms the rotating magnetic field whose direction is controlled based on the transmitted control signal. The capsule main body 6 is freely rotated by a magnet which will be described later, magnetically acted upon by the rotating magnetic field formed by the magnetic guiding device 5. Thus, the capsule medical apparatus 1 is guided in the advancing direction in the body cavity by a thrust generating unit, which will be described later, and obtains the thrust force.

The control signal for controlling the capsule medical apparatus 1 is modulated by carriers having a predetermined frequency through a transmitting circuit in the PC main body 11, and is transmitted as electric waves from the extra-body antenna 14.

The capsule medical apparatus 1 receives the electric waves via a radio antenna 21, which will be described later. Then, the control signal is demodulated and is outputted to the circuits.

The control device 3 receives, via the extra-body antenna 14, information (data) signal such as a video signal transmitted from the radio antenna 21 in the capsule medical apparatus 1, and displays the received signal on the monitor 13.

Next, a description is given of the detailed structure of the capsule medical apparatus 1 according to the first embodiment with reference to FIG. 2 and FIGS. 3A to 3C. According to the first embodiment, the capsule medical apparatus can perform only the examination (observation).

The capsule medical apparatus 1 mainly comprises: the radio antenna 21 which receives and transmits the electric waves to/from the control device 3; a radio receiving and transmitting circuit 22 which executes the signal processing of the electric waves received and transmitted by the radio antenna 21; an illuminating device 23 such as an LED (Light Emitting Diode) which generates illumination light for illumination in the body cavity; an observing device 24 which captures an optical image of the body cavity illuminated by the illumination light from the illuminating device 23 and picks up the image; a digital signal processing circuit 25 which performs the digital signal processing of an image pick-up signal obtained by picking up the image by the observing device 24; a battery unit 26 storing a battery 26a such as a battery which supplies power; and a switch 27 which turns on/off the source power supplied from the battery unit 26.

The radio receiving and transmitting circuit 22 selectively extracts and detects carriers of the electric waves from the control device 3, which is received by the radio antenna 21, demodulates the control signal, and outputs the demodulated signal to the circuits. Further, the radio receiving and transmitting circuit 22 modulates, by the carrier with a predetermined frequency, the information (data) signal such as the video signal from the circuits, and transmits the modulated signal as the electric waves from the radio antenna 21.

The observing device 24 comprises: an objective optical system 31 which captures the optical image; an image pick-up sensor 32 such as a CMOS (Complementary Metal-Oxide Semiconductor) sensor and a CCD, which is arranged to the image forming position of the objective optical system 31 and picks up the formed optical image; and an image pick-up driving circuit 33 which drives the image pick-up sensor 32.

The digital signal processing circuit 25 comprises: a digital video signal processing circuit (hereinafter, referred to as a video signal processing circuit) 34 which performs the signal processing of the image pick-up signal obtained by picking up the image by the image pick-up sensor 32 and converts the picked-up signal into a digital video signal; and a digital compression processing circuit (hereinafter, referred to as a compression processing circuit) 35 which compresses the digital video signal converted by the video signal processing circuit 34.

The battery unit 26 supplies the source power from the battery 26a to the illuminating device 23, the digital signal processing circuit 25, and the radio receiving and transmitting circuit 22, via the switch 27. The source power is supplied from the battery 26a to the observing device 24 via the digital signal processing circuit 25.

As mentioned above, the capsule medical apparatus 1 includes a permanent magnet (hereinafter, simply referred to as a magnet) 36 for magnetic action to the rotating magnetic field formed by the magnetic guiding device 5. The magnet 36 used here is a permanent magnet such as a neodymium magnet, samarium-cobalt magnet, ferrite magnet, iron chromium cobalt magnet, platinum magnet, alnico (AlNiCo) magnet, and the like. A rare-earth system magnet such as the neodymium and samarium-cobalt magnet has strong magnetic force and has a merit that the magnet included in the capsule is small. On the other hand, the ferrite magnet has a merit that it is inexpensive. Further, the platinum magnet has excellent resistance to corrosion and is suitable for medical use.

The magnet 36 included in the capsule main body 6 is not limited to the permanent magnet and may be one containing a coil. In the capsule main body 6 in this case, the current from a power supply such as a built-in battery may generate the magnetic force in the coil or the coil may be magnetized by power that is temporarily stored in a built-in condenser. Further, the capsule main body 6 may generate the power by one inner coil and another coil may be magnetized by storing the power in the one coil. In the capsule main body 6 in this case, the capacity of the inner battery is not limited and the capsule main body 6 can operate for a long time. A coil for generating power may be shared with a coil for the magnet.

Figure 3C:
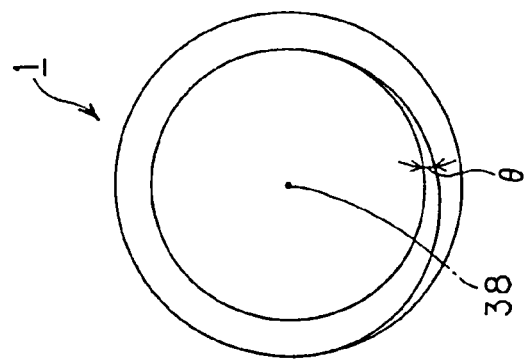
FIGS. 3A to 3D show the structure of the capsule medical apparatus.
Figure 3A:
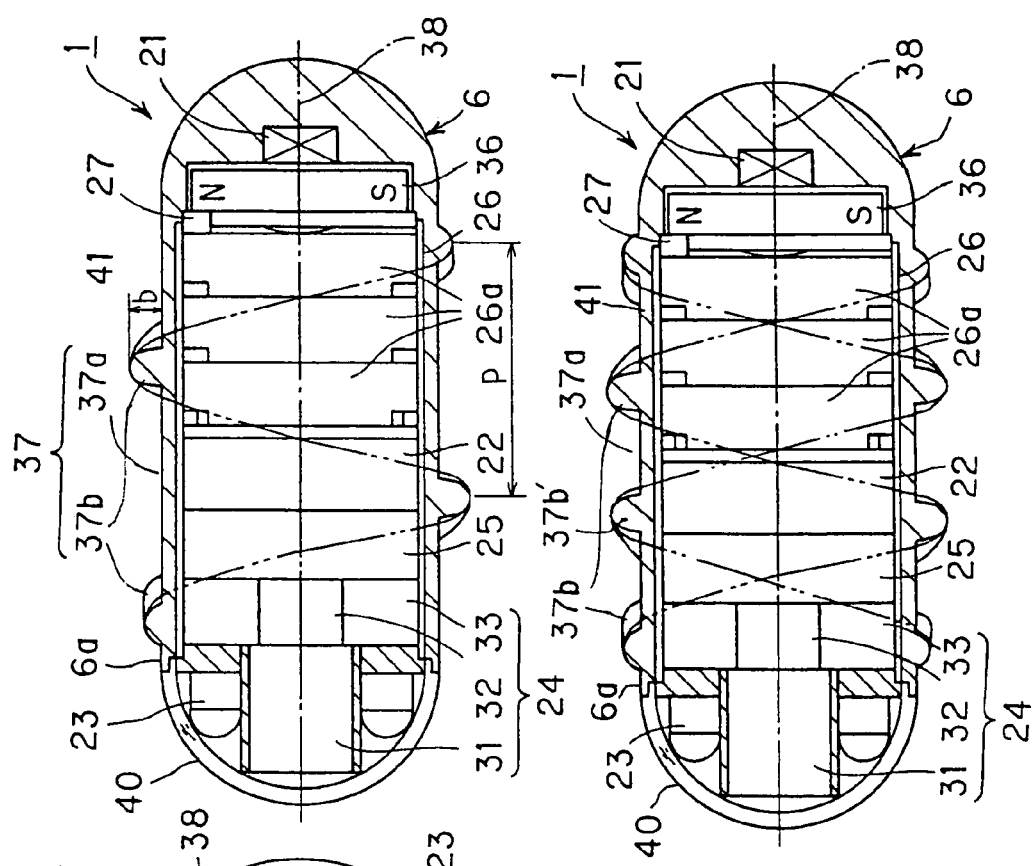
Figure 3B:
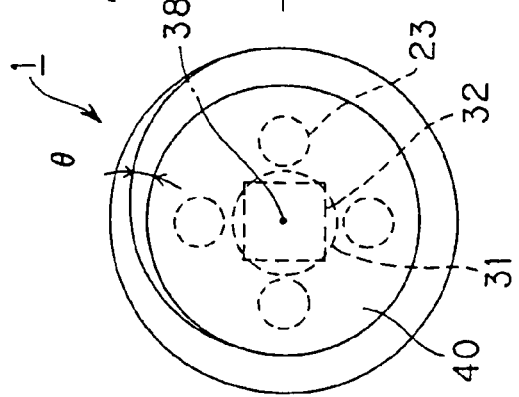

Referring to FIGS. 3A to 3C, the capsule medical apparatus 1 has the cylindrical capsule main body 6 which is airtightly covered by a transparent edge cover 40 and a main body exterior member 41 airtightly connected to the edge cover 40. The capsule main body 6 contains units such as the illuminating device 23 and the observing device 24 therein. Specifically, in the capsule medical apparatus 1, the objective optical system 31 forming the observing device 24 is arranged to the center of the edge of the capsule main body 6, and the image pick-up sensor 32 is arranged to the image forming position of the objective optical system 31.

The image pick-up driving circuit 33 is arranged around the image pick-up sensor 32. The digital signal processing circuit 25 is arranged to the base end sides of the image pick-up driving circuit 33 and the image pick-up sensor 32. The radio receiving and transmitting circuit 22 is arranged to the base end side of the digital signal processing circuit 25.

The illuminating device 23 is arranged around the objective optical system 31 so as to illuminate the forward portion of the capsule main body 6 via the edge cover 40. The illuminating device 23 shown in FIG. 2 comprises four LEDs as shown in FIG. 3B.

The battery unit 26 is arranged to the rear portion of the radio receiving and transmitting circuit 22, and the three batteries 26a such as button batteries are stored in the battery unit 26. The switch 27 is connected to the battery unit 26 by an external operation (not shown) and then the power fed by the power supply is supplied via the switch 27. On the rear portion side of the battery unit 26, the magnet 36 is arranged and the radio antenna 21 is arranged.

In the capsule medical apparatus 1, the above components are reinforced and are held by a cylindrical member such as a metal ring reinforcing member and are arranged in the main body exterior member 41. The capsule medical apparatus 1 has the size to enable the patient 3 to easily swallow the capsule main body 6.

In the capsule medical apparatus 1, the magnet 36 is arranged to have the magnetizing direction in the direction perpendicular to the longitudinal central axis of the capsule main body 6. Thus, in the capsule medical apparatus 1, the magnet 36 acts to the rotating magnetic field generated by the magnetic guiding device 5 and then the operation of the magnet 36 rotates the capsule main body 6.

In the capsule medical apparatus 1, a thrust generating unit 37 is arranged to the outer peripheral surface of the capsule main body 6. The thrust generating unit 37 has a spiral projected portion 37b which is spirally projected from a cylindrical outer peripheral surface (base surface) 6a of the capsule main body 6 and is in contact with the inner wall of the body cavity (corresponding to a spiral contact portion). A spiral groove 37a is arranged between the adjacent spiral projected portions 37b so that the fluid such as gas in the body cavity or body fluid can continuously flow. As will be described later, the spiral projected portion 37b may be a projected portion that is spiral-shaped.

According to the first embodiment, the height or pitch of the spiral projected portion 37b is set to have the proper value as will be described later. Further, the thrust generating unit 37 is formed to optimal and efficiently advance by the rotation. An angle θ formed between both ends of the spiral projected portion 37b, namely, the rising portion and the falling portion of the spiral projected portion 37b from the outer peripheral surface 6a is set to have a proper value.

Referring to FIG. 3A, a height b of the spiral projected portion 37b (the peak or top of the spiral projected portion 37b formed from the outer peripheral surface 6a having the spiral projected portion 37b) is 2 mm or less when the outer diameter of the capsule main body 6 is 10 mm. When the outer diameter of the capsule main body 6 is 8 mm, the height b of the spiral projected portion 37b is set to be 3 mm or less. A pitch p of the spiral projected portion 37b is 10 mm or more. Upon rotating the capsule main body 6 provided by the outer peripheral surface 6a, owing to the spiral projected portion 37b having the above-described pitch, the capsule main body 6 greatly advances.

The rising angle or falling angle θ (from the outer peripheral surface 6a) at the end portion of the spiral projected portion 37b is set to 45° or less, and is formed to smoothly rise or fall.

Figure 3D:
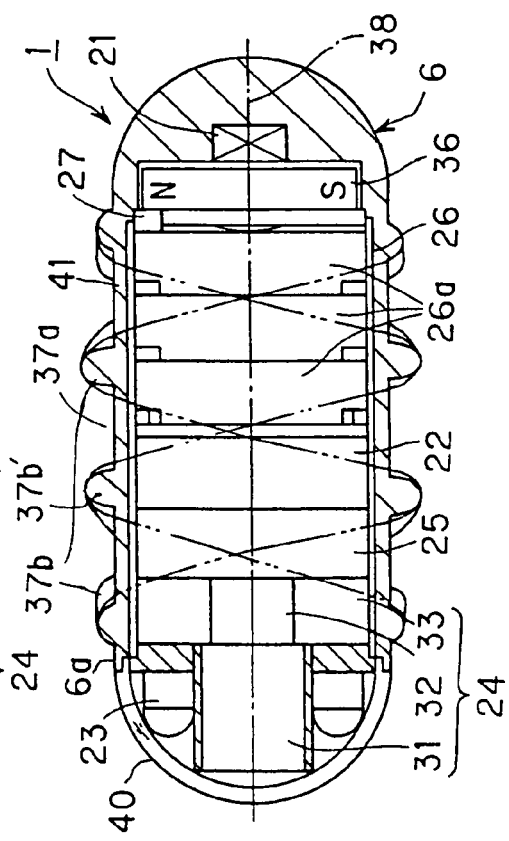

Referring to FIGS. 3A to 3C, for the purpose of a brief description, the spiral projected portion 37b with a one-spiral screw structure is shown. Referring to FIG. 3D, the spiral projected portion 37b has a two-spiral screw structure and the capsule main body 6 is rotated, the capsule main body 6 with the two-spiral screw structure may greatly advance as compared with that with the one-spiral screw structure. Referring to FIG. 3D, a spiral projected portion 37b' is similarly formed between the spiral projected portions 37b with the one-spiral screw shown in FIG. 3A.

In the capsule medical apparatus 1 with the above-mentioned structure, the spiral projected portion 37b is in contact with the inner wall of the body cavity in accordance with the rotation of the capsule main body 6. Further, the capsule medical apparatus 1 advances or returns by efficiently converting the rotating force to the thrust. The cross section of the spiral projected portion 37b is optimal so that capsule medical apparatus 1 is smoothly in contact with the inner wall of the body cavity and the capsule medical apparatus 1 advances with the stable contact frictional force with the mucous membrane.

In the capsule medical apparatus 1, the capsule main body 6 rotates and simultaneously changes the advancing direction so that the rotating plane of the magnet 36 substantially matches the rotating plane of the rotating magnetic field in accordance with the rotation of the rotating magnetic field.

If the center of gravity of the capsule medical apparatus 1 does not substantially match the longitudinal central axis 38 of the capsule main body 6, the capsule main body 6 is subjected to eccentric motion (jiggling) and the unnecessary movement is generated.

According to the first embodiment, in the capsule medical apparatus 1, the heaviest battery 26a such as the button battery is arranged on the longitudinal central axis 38, the center of the magnet 36 is arranged onto the longitudinal central axis 38 of the capsule main body 6, and thus the center of gravity of the capsule medical apparatus 1 substantially matches the longitudinal central axis 38 of the capsule main body 6. Consequently, the capsule medical apparatus 1 can smoothly move to the target portion in the luminal portion without the unnecessary movement such as the eccentric motion (jiggling) of the capsule main body 6.

As mentioned above, according to the first embodiment, the height, interval, rising angle, the projecting shape of the spiral projected portion 37b, and the like are properly set so that the capsule medical apparatus 1 stably and smoothly advances by acting the rotating magnetic field to the capsule medical apparatus 1. Further, the rotating velocity and the magnetic torque of the rotating magnetic field are set to be within the proper range.

In order to properly set the shape of the above-mentioned spiral projected portion 37b, the height of the spiral projected portion 37b is changed, the capsule main body (hereinafter, abbreviated to a capsule), as a sample, having the magnet is prepared, and the experiment for obtaining necessary measurement data by using the following device is performed. In this case, the experiment will be described based on the driving principle diagram shown in FIG. 4.

Figure 4:
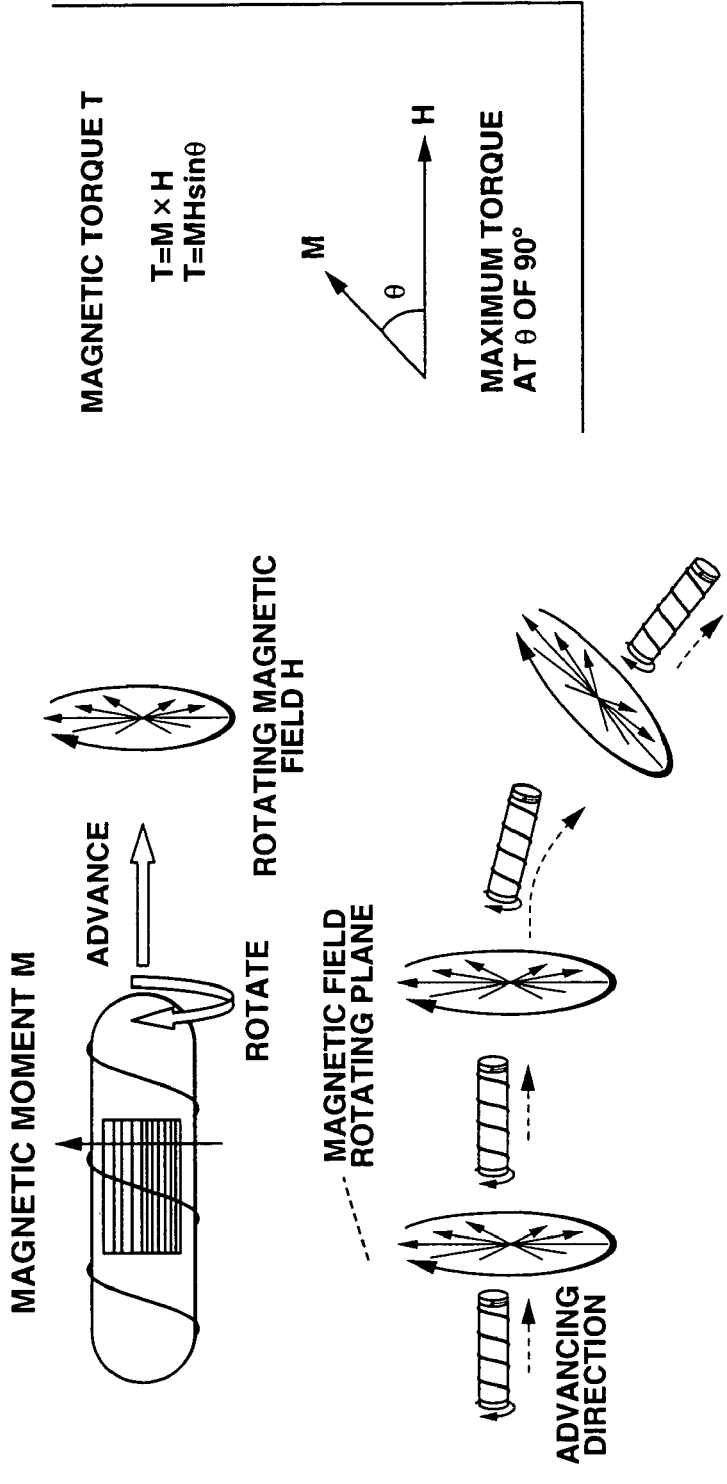

FIG. 4 shows the driving principle for generating the rotating magnetic field by a rotating magnetic field generating device 90 and for rotating and advancing the capsule. Referring to FIG. 4, a permanent magnet is magnetized in the direction perpendicular to the longitudinal direction of the capsule and is included in the capsule. The rotating magnetic field is applied from the outside of the capsule and the rotating magnetic field rotates the permanent magnet together with the capsule by the magnetic torque exerted to the permanent magnet.

As a result of rotation, the capsule with the spiral structure arranged to the outer peripheral surface of the capsule advances by converting the rotating force into the thrust. Further, the advancing direction can be controlled by changing the rotating plane of the rotating magnetic field. Referring to FIG. 4, the magnetic torque is designated by reference symbol T, the magnetic moment of the permanent magnet is designated by reference symbol M, and vector of the rotating magnetic field is designated by reference symbol H. Then, the magnetic torque T is expressed as the vector product of the magnetic moment M and the rotating magnetic field H.

Figure 5A:
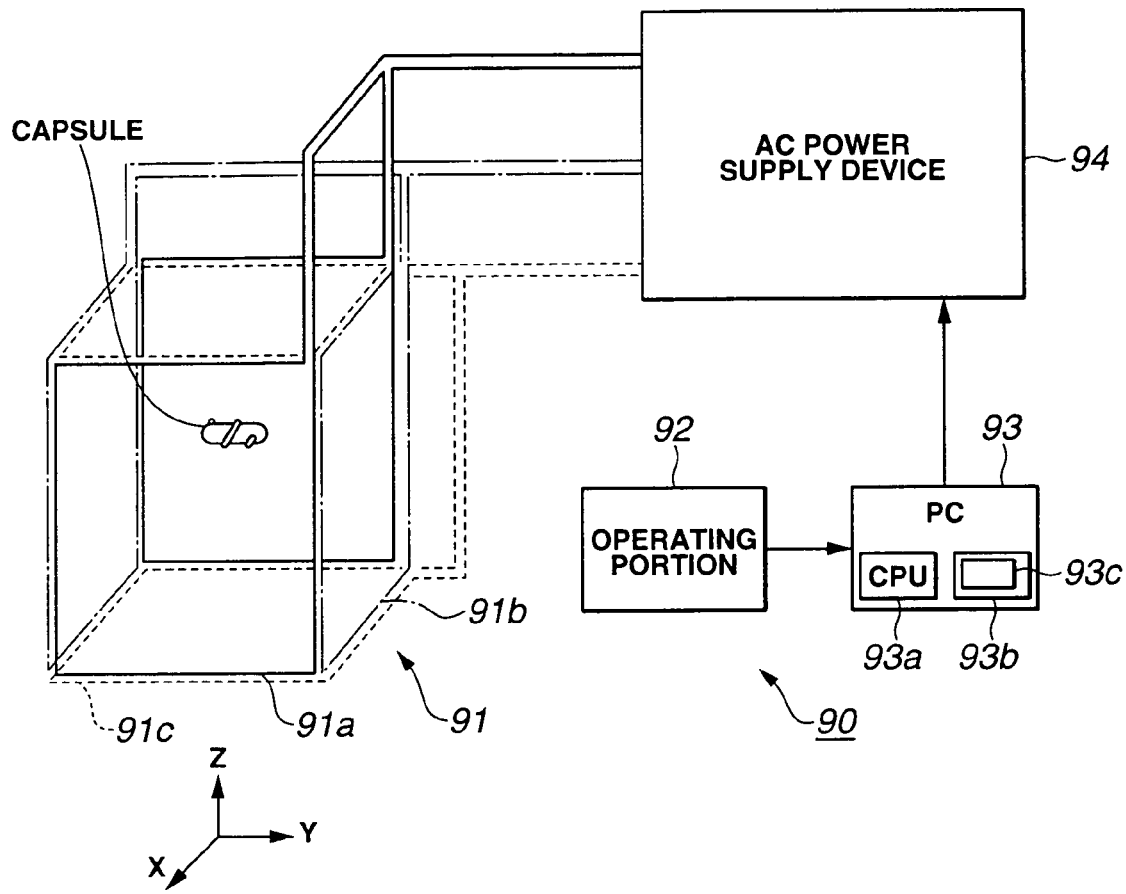
FIG. 5A is a diagram showing the schematic structure of a rotating magnetic field generating device.

FIG. 5A shows the schematic structure of the rotating magnetic field generating device 90 which is also used as the magnetic guiding device 5. Referring to FIG. 5A, the rotating magnetic field generating device 90 has a triaxial Helmhoz coil 91 (91a, 91b, and 91c) which can generate an AC magnetic field in the perpendicular x, y, and z directions. The output values and phases of the three AC currents from an AC power supply device 94 are controlled via a PC 93 for controlling the operating input of an operating portion 92 having the operating means such as a joystick, thus to control the direction, rotating plane, and rotating direction of the combined magnetic field generated by the triaxial Helmhoz coil 91. Further, the magnetic field is applied by changing the strength or frequency of the rotating magnetic field to the capsule arranged in the triaxial Helmhoz coil 91.

Referring to FIG. 5A, the schematic structures of the Helmhoz coils 91a, 91b, and 91c for generating the substantially uniform magnetic fields in the x, y, and z directions are shown by a solid line, a one-dotted line, and a dotted line.

Figure 6:
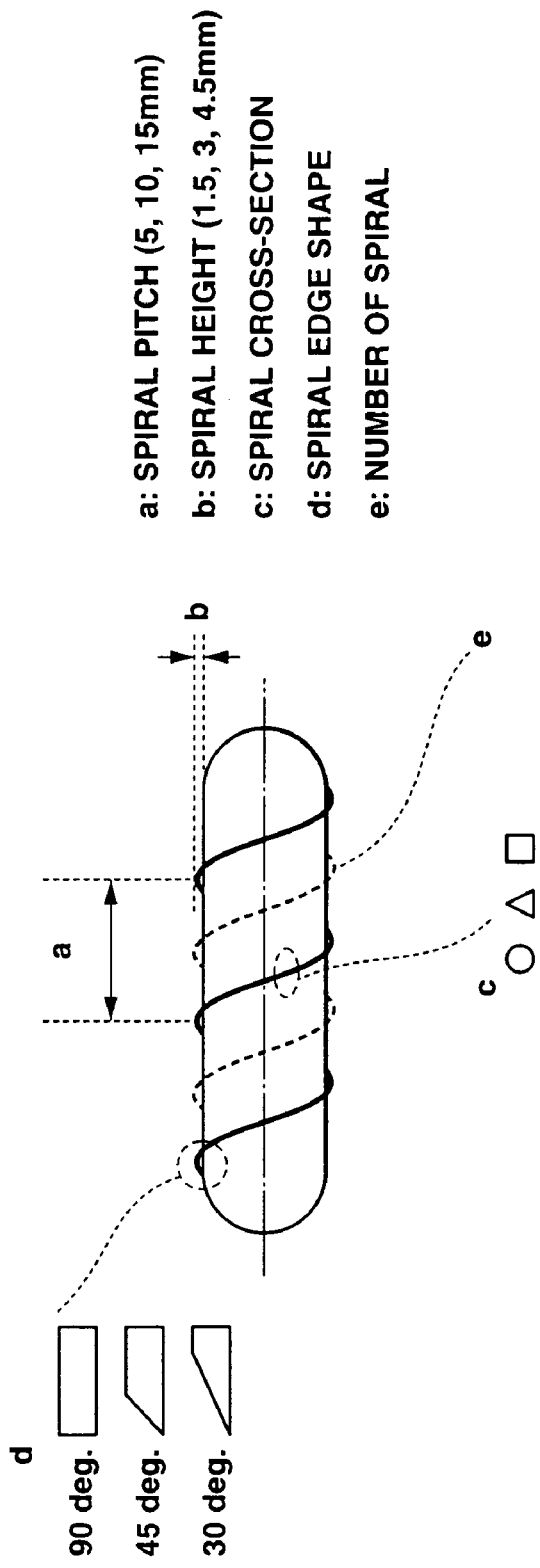

FIG. 6 shows the outline of examining items for setting the spiral shapes for obtaining the proper thrust.

Referring to FIG. 6, the spiral shape greatly influences on the driving characteristic of the capsule so as to convert the rotation to the thrust with the spiral structure. Therefore,
a: spiral pitch [5, 10, and 15 mm],
b: spiral height [1.5, 3, and 4.5 mm],
c: spiral cross-section [circular, triangular, and square],
d: spiral edge shape (rising and falling shape) [90°, 45°, and 30°],
e: number of spiral (spiral interval) [1 spiral, 2 spirals, 4 spirals, and 12 spirals], and the like are changed, thus to obtain the measurement data of the advancing velocity and the load torque.

Figure 7:
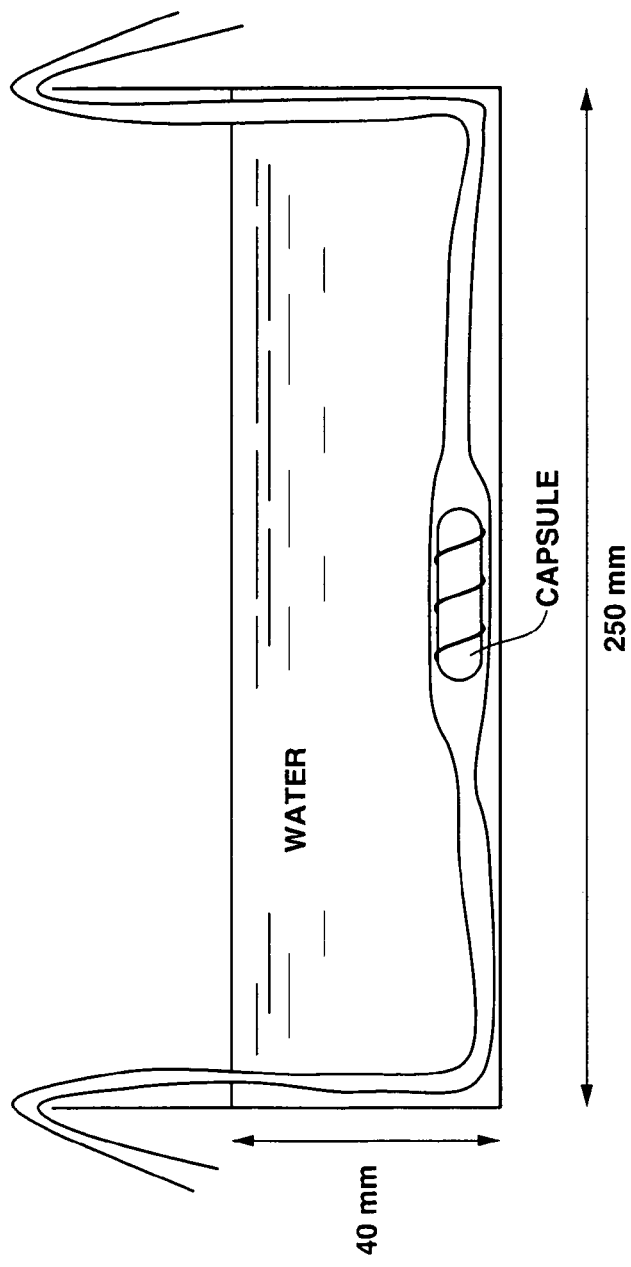

In this case, upon measuring the advancing velocity, referring to FIG. 7, a silicon rubber tube is put in a water cistern, the capsule is inserted in the tube in the water cistern, the water is run to the height of 40 mm, and the situation is set to the similar state in which the capsule is inserted in the luminal portion of the body cavity.

Further, the advancing velocity is measured by changing the rotating frequency of the capsule, namely, the frequency of the rotating magnetic field, the friction level (quantity of silicon oil run in the tube), and the adhesion degree (water depth) of the capsule and the tube.

In order to confirm that the examination using the silicon rubber tube is pseudo to the state in which the capsule is inserted in the luminal portion of the body cavity, it is checked by using the pig organ (small intestine or large intestine) (not shown) that the same situation as that using the silicon rubber tube is indicated and the capsule having the optimal shape stably advances.

Figure 8:
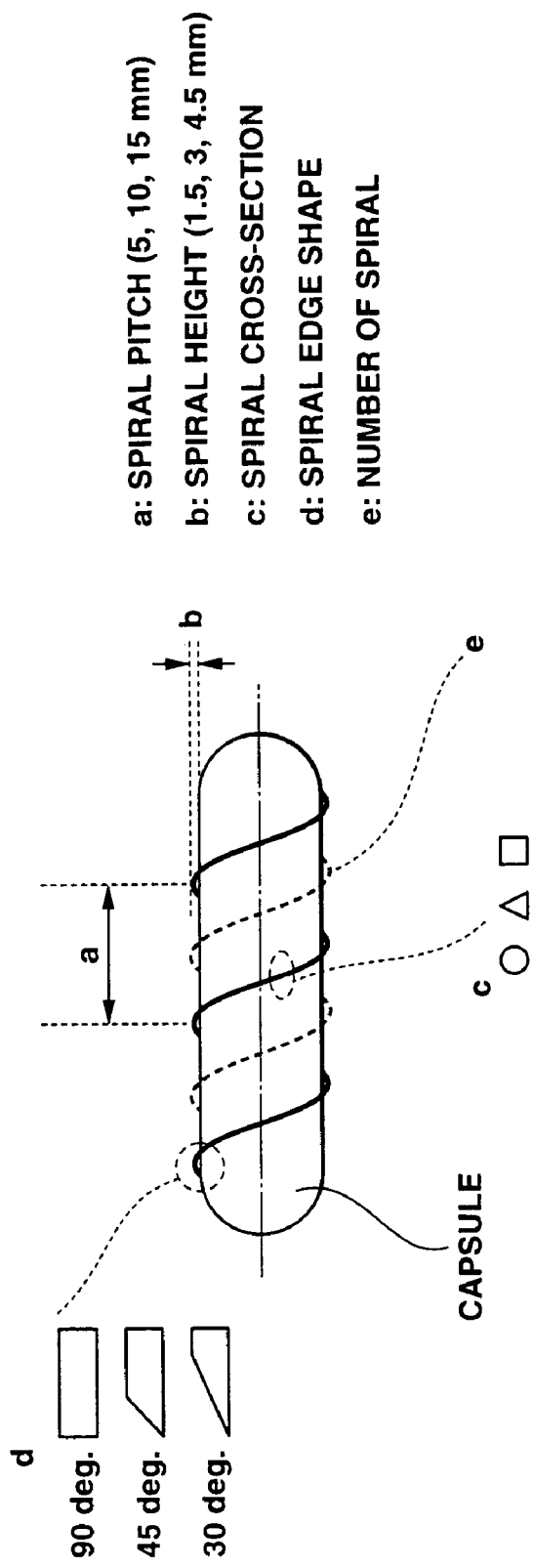

FIG. 8 shows the spiral shape used for the examination. Here, the capsule having the diameter of 11 mm and the length of 40 mm are prepared by changing the conditions a (: spiral pitch) to e (number of spiral) as shown in FIG. 6 and the advancing velocity is measured by changing the rotating frequency and the like.

Figure 9:
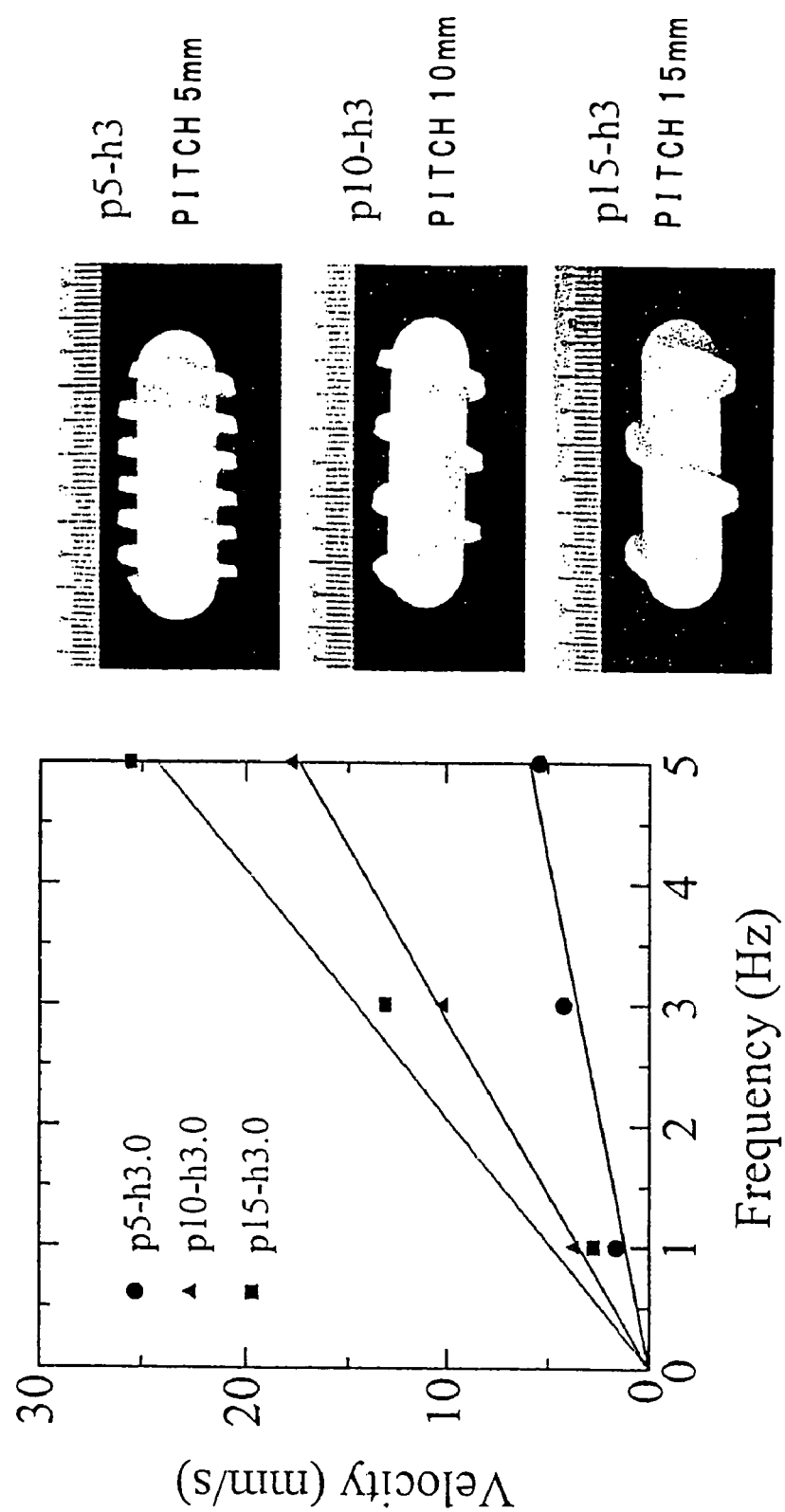

FIG. 9 shows the measurement data which measures the advancing velocity by changing the rotating frequency in the case of three capsules with the changed spiral pitches. Here, the pitch is 5 mm, 10, mm, and 15 mm. The spiral height in this case is 3 mm.

Based on the measurement data shown in FIG. 9, the measured result is obtained that the advancing velocity is increased with the large pitch, as compared with the small pitch (5 mm). As a result, preferably, the pitch is 10 mm or more.

FIG. 10 shows the measurement data which measures the advancing velocity by changing the rotating frequency in the three capsules having the changed spiral heights. Here, the pitch is 15 mm and the height is 1.5 mm, 3 mm, and 4.5 mm. The condition in this case is that the oil quantity of the silicon in the tube shown in FIG. 7 is 60 ml.

As the measurement result, preferably, the spiral height is 3 mm. In the case of the spiral height (4.5 mm) higher than 3 mm, the advancing velocity reduces. In the case of the spiral height of 1.5 mm, the advancing velocity reduces. Therefore, the spiral height is preferably 3 mm.

Meanwhile, referring to FIG. 11, the spiral height is 3 mm and 1 mm and the quantity of oil changes. Further, even in the case of rotating velocity of 1 Hz, the advancing velocity is measured. Based on the measurement data, even in the case of the low spiral-height (1 mm), the advancing velocity increases depending on the quantity of oil, as compared with the proper spiral-height (3 mm) in FIG. 10.

Based on the measurement data shown in FIGS. 10 and 11, preferably, the spiral height is estimated to be 3 mm or less.

Figure 12:
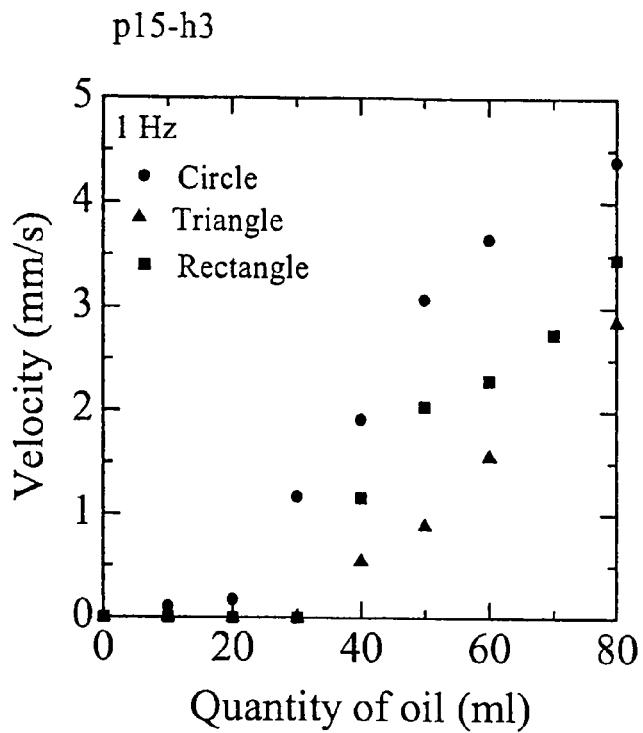

FIG. 12 shows the measurement data in the case of changing the spiral cross-section. That is, referring to FIG. 12, the spiral pitch is 15 mm, the spiral height is 3 mm, and the spiral cross-section is circular, triangular, and square. Then, the measurement data of the advancing velocity is shown by changing the quantity of oil.

Based on the measured result, the advancing velocity increases with the circular spiral.

Figure 13:
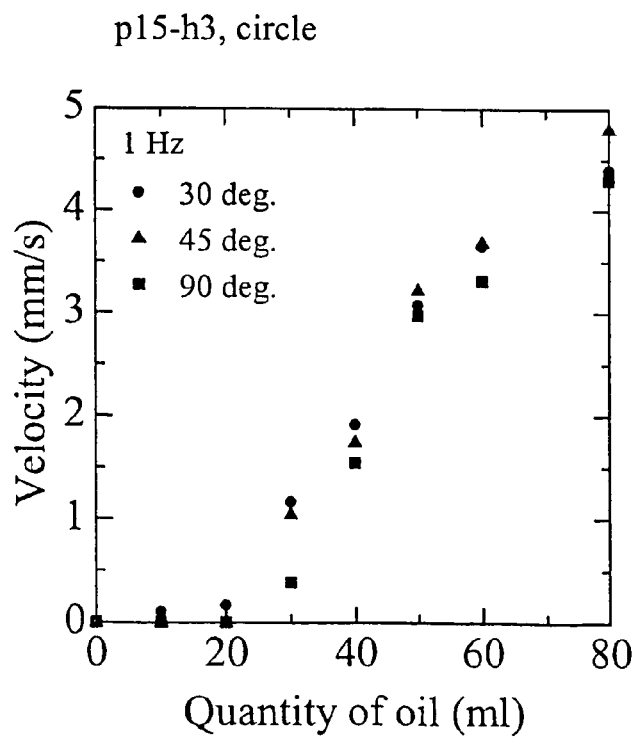

FIG. 13 shows the measurement data in the case of changing the spiral edge (end portion) shape. That is, referring to FIG. 13, the spiral pitch is 15 mm, the spiral height is 3 mm, and the spiral cross-section is circular. Then, the inclining angle of the spiral rising (falling) is set to 30°, 45°, and 90°. Then, the measurement data of the advancing velocity is shown by changing the quantity of oil.

Based on the measurement result, preferably, the inclining angle is 45° or less.

FIG. 14 shows the measurement data in the case of changing the number of spirals. That is, referring to FIG. 14, the spiral pitch is 15 mm, the spiral height is 1 mm, and the spiral cross-section is circular. Then, the number of spirals is set to be 1, 2, 4, and 12. Further, the measurement data of the advancing velocity is shown by changing the quantity of oil.

Based on the measured result, the advancing velocity increases with the multi-spiral, as compared with one spiral. However, in the case of the 12 spirals, the advancing velocity reduces as compared with 11 spirals or less (four spirals).

Therefore, based on the measurement result, the advancing velocity increases in the case of forming the capsule like a multi-spiral screw having two spirals or more and 10 spirals or less.

Figures 15A, 15B:
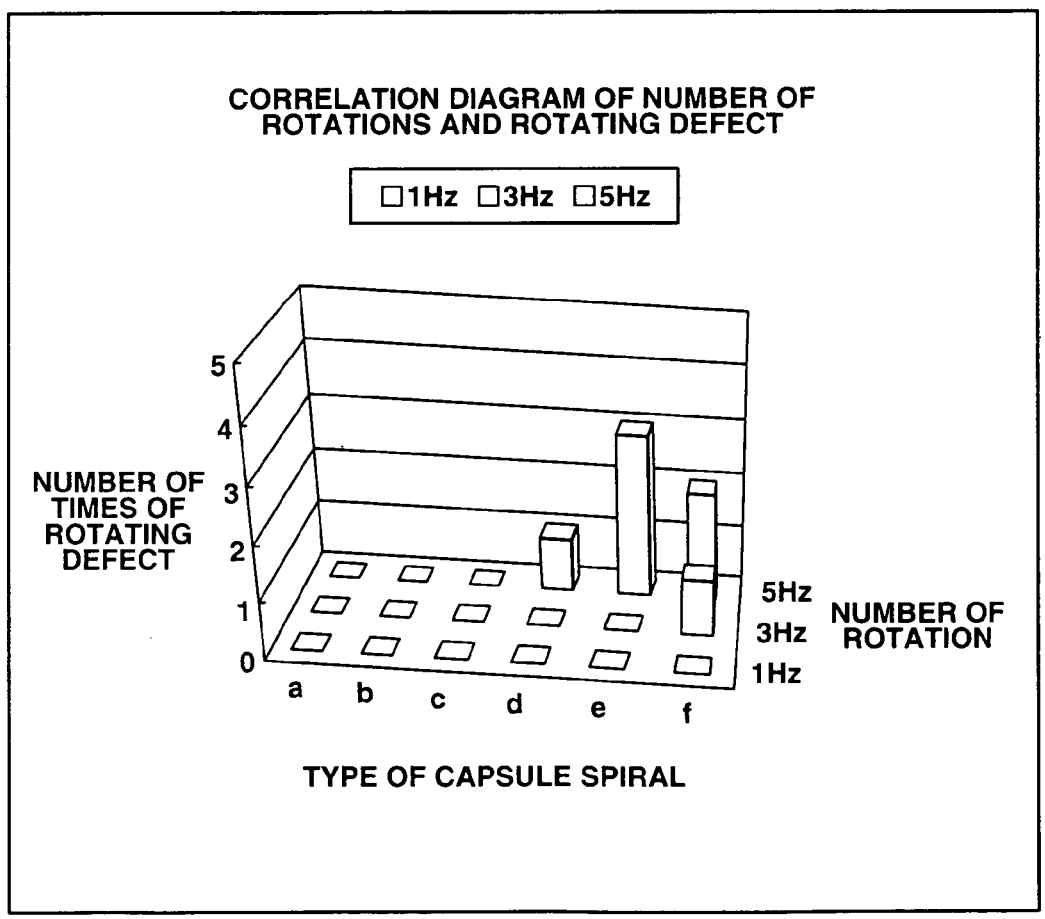
FIGS. 15A and 15B are diagrams showing the measurement data which is measured by changing the number of rotation, depending on the different spiral heights.

FIGS. 15A and 15B show the measurement data of the number of times of the rotating defects (rotating defect that the capsule does not follow the rotation) by preparing the capsule with the changed spiral pitch and height and by changing the frequency of the rotating magnetic field. FIG. 15A shows a table and FIG. 15B shows a graph of main data.

Referring to FIG. 15A, based on the measurement data of the spiral types a to f, when the spiral height is 3 mm or less, the occurrence ratio of the rotating defect is low up to the rotating velocity of 5 Hz. However, when the spiral height is 4.5 mm, the occurrence ratio of the rotating defect is high unless at the rotating velocity of 3 Hz or less.

Therefore, preferably, the rotating velocity is 5 Hz or less so as to rotate the capsule with the suppressed occurrence ratio of rotating defect, based on the measurement data shown in FIG. 15A.

The torque is measured by using a torque measuring device 95 shown in FIG. 16.

The torque measuring device 95 shown in FIG. 16 obtains data on the capsule having the shape of the proper thrust generating unit and proper data on the magnetic torque. The torque measuring device 95 comprises a body luminal portion pseudo device 96 which sandwiches from the top and bottom sides, by a water bag 96b, a pseudo body luminal portion 96a which is pseudo by the pig organ (specifically, the small intestine). The top portion of the water bag 96b is those of 1000 ml, 2000 ml, and 3000 ml, that is, the influence on the pseudo body luminal portion 96a is changed.

The capsule is inserted in the pseudo body luminal portion 96a. One end of a rod 97 is fixed to the rear end of the central axis of the capsule. A torque gage 99 is connected to the other end of the rod 97 via a bearing portion 98 for rotatably supporting the rod 97. The torque acting on the capsule is measured by the torque gage 99. The bearing portion 98 comprises a hollow cylindrical member 98a and a ball bearing 98b which is engaged with the hollow portion of the cylindrical member 98a and rotatably supports the rod 97.

Based on the torque measurement, the torque necessary for pseudo-rotating the capsule in the body cavity.

The capsules with the spiral and without spirals are used. In this case, the capsule has the spiral pitch of 12.5 mm and the height of 1 mm, 1.5 mm, and 2 mm and contains a plastic material. Further, the capsule has the spiral pitch of 15 mm and the height of 3 mm and contains rubber. Furthermore, the capsule has the pitch of 15 mm and the height of 1 mm (single spiral) and contains vinyl (wiring) with two spirals.

The magnetic torque is measured six times including three times of clockwise rotation and three times of anticlockwise rotation. Two portions of small intestine with different diameter are measured (with the inner diameter of not over 10 mm and not over 15 mm).

Figure 17B:
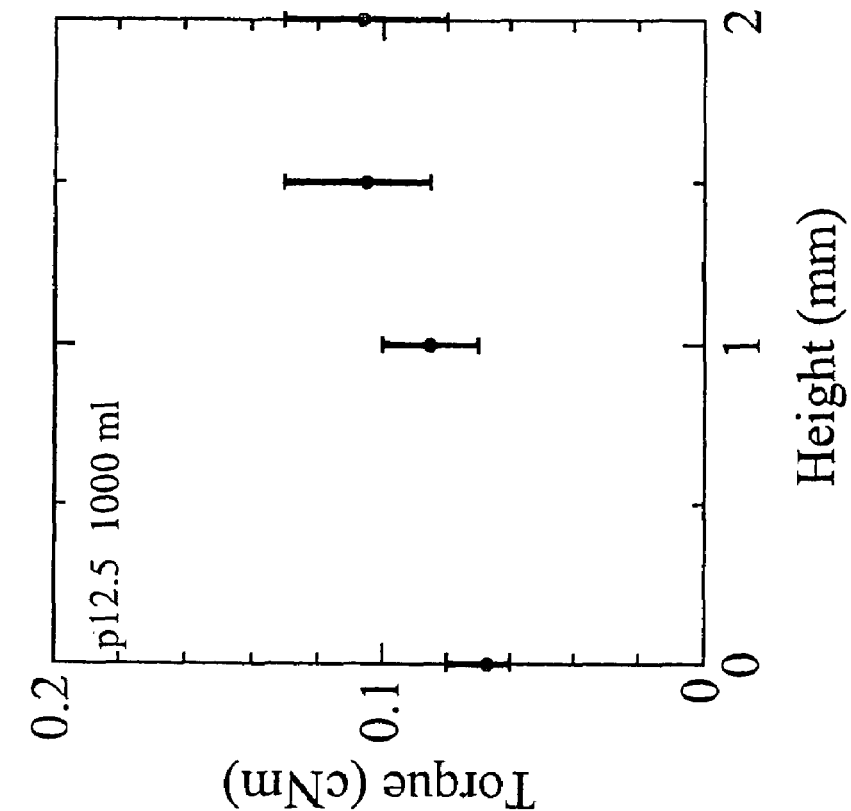
FIGS. 17A and 17B are diagrams showing the measurement data of torque which is required for rotation, depending on the different spiral heights.
Figure 17A:
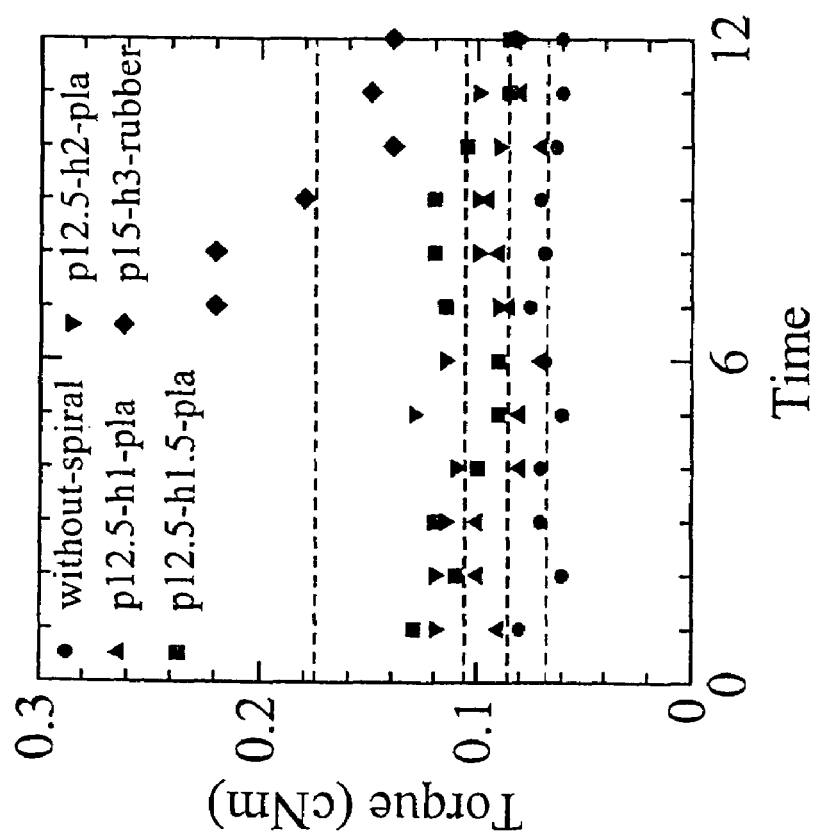

FIGS. 17A and 17B show the plastic and rubber capsules with the spiral and without the spiral. FIG. 17A individually shows the result of measuring the magnetic torque necessary for rotation and FIG. 17B shows the magnetic torque in the case of changing the height with the pitch of 12.5 mm.

Based on the measurement result shown in FIG. 17A, the lowest torque necessary for rotating the capsule is 0.06 cNm or more. If the lowest torque is 0.2 cNm or more, any capsule can be rotated. If the capsule is stably rotated, it is considered that the torque of 0.4 to 0.6 cNm is generated with the two or three times of the safety factor.

Referring to FIGS. 18A and 18B, the capsule with the spiral and the capsule without the spiral are used. Further, the spiral pitch is 15 mm, the height is 1 mm (single spiral), and the vinyl (wiring) with two spirals is used. Then, based on the measurement shown in FIG. 17A (refer to FIG. 18A), the result is described with the number of spirals (refer to FIG. 18B).

Referring to FIG. 18A, the number of spirals increases and the torque further increases. In this case, the lowest torque is 0.06 cNm or more and 0.2 cNm or more to rotate the capsule having the measurement result shown in FIG. 17A and, then, the capsule can be rotated in both the cases.

Figure 19A:
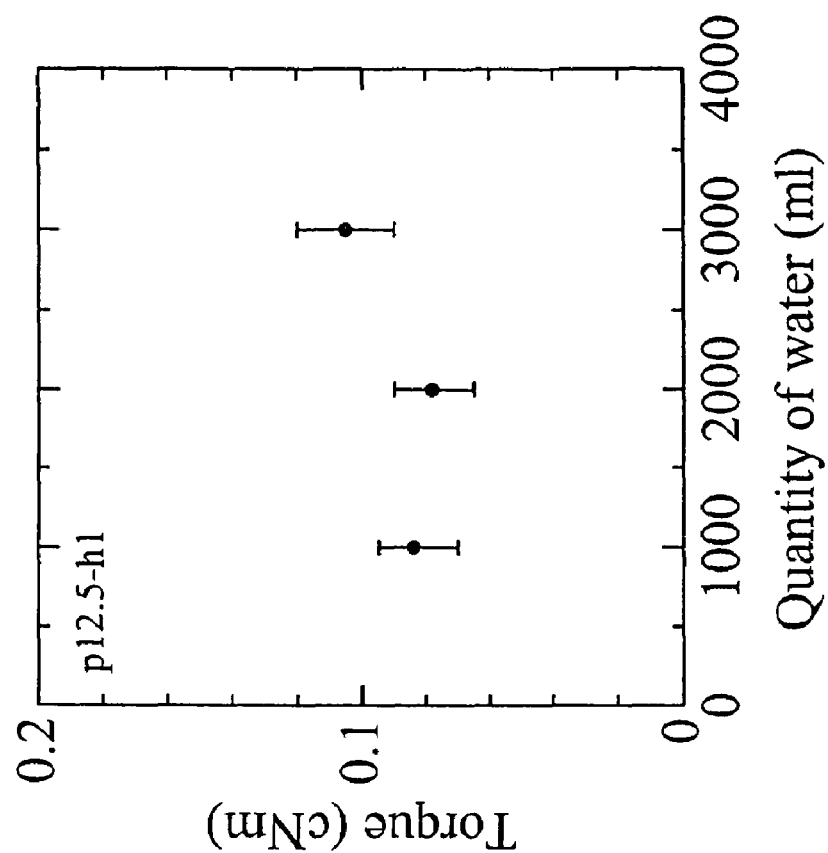
FIGS. 19A and 19B are diagrams showing the measurement data of torque which is required for rotation upon changing the solution amount of a water package.
Figure 19B:
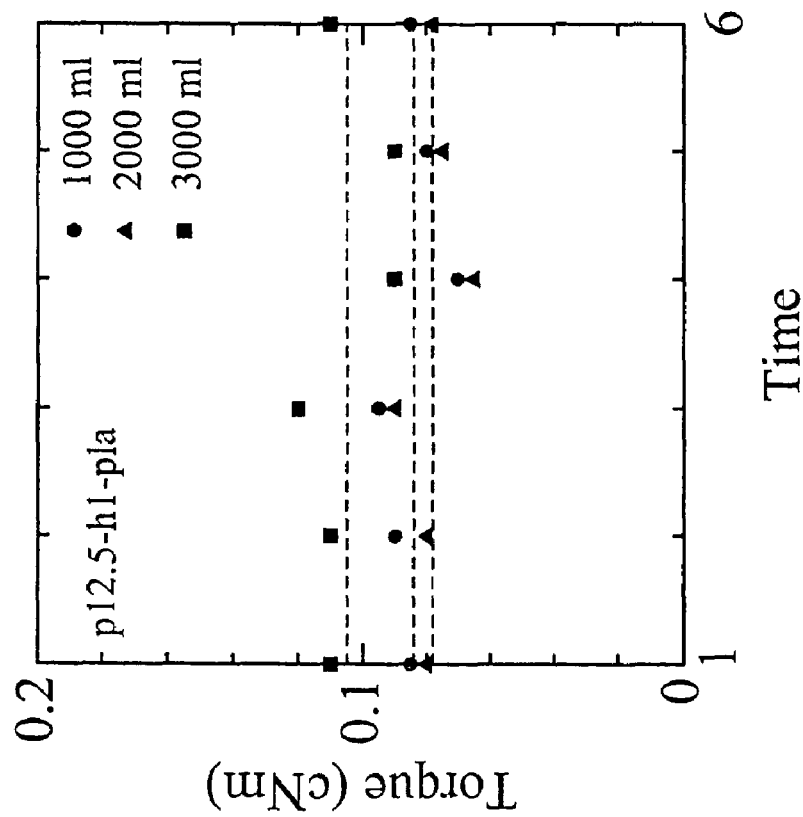

Referring to FIGS. 19A and 19B, the capsule has the spiral pitch of 12.5 mm and the height of 1 mm. Then, the torque is measured in the case of changing the top water bag 96b shown in FIG. 16 to 1000 ml, 2000 ml, and 3000 ml (refer to FIG. 19A). The result is described with the relationship of the water amount (refer to FIG. 19B).

In the case of changing the water amount, the measurement result indicates the torque value does not greatly change.

FIG. 20 shows the magnetic torque level upon applying the external magnetic field (here, 150 Oe) by the magnetic moment depending on the magnet size. In this case, since the magnet needs to be housed in the capsule as the body cavity inserting portion that is inserted in the body cavity. Among magnet sizes A to D shown in FIG. 20, the magnet with the size (volume) D is preferable. The magnetic torque generated in this case is 1 cNm and preferably the magnetic torque of 1 cNm or less. When there are no regulations such as the volume, weight, and costs of the magnetic field generating means, the magnetic torque of 1 cNm or more may be generated.

The above measurements are summarized as follows.

(1) Examination and summary for detecting the shape of the thrust generating unit suitable to stably advance the capsule as the body cavity inserting portion in the body cavity such as the small intestine or large intestine:

In order to determine the shape of the spiral portion for generating thrust, the examination is performed by using the pig organ and the silicon sheet for the following parameters. Consequently, the optimum values and the trend are found based on experiment data every parameter.

I. Parameter Type a. Spiral Pitch [5, 10, and 15 mm]

The capsule with the spiral pitch of 5 mm is slowly rotated. The capsule with the spiral pitch of 10 and 15 mm is rotated faster.

b. Spiral Height [1.5, 3, and 4.5 mm]

The capsule with the spiral height of 3 mm is rotated fastest. However, if the quantity of oil is small (sliding performance with the body wall is poor), the capsule with the spiral height of 1.5 mm is rotated faster in many cases.

c. Spiral Cross-Section [Circular, Triangular, and Square]

Irrespective of the quantity of oil (performance for sliding to the body wall), the circular cross-section is best.

d: Spiral Edge Shape (Rising and Falling Shape) [90°, 45°, and 300]

If the amount of oil (performance for sliding to the body wall) is small, the capsule with the spiral edge shape at the angle of 30° is preferable. Irrespective of the quantity of oil, the capsule with the spiral edge shape at angle of 90° is the worst.

e: Number of Spiral (Spirals) [1 Spiral, 2 Spirals, 4 Spirals, and 12 Spirals]

The capsule with the 1 spiral is the worst and the capsule with the 12 spirals is secondarily worst. The capsule with the 2 spirals and 4 spirals is good.

II. Optimum Value and Trend a. When the spiral pitch is 10 mm or more and is more than it, the thrust of the capsule is higher. The stable contact state requires the correlation with the entire length of the capsule and, preferably, the pitch has the entire length or less. For example, if the entire length of the capsule is 40 mm, the pitch is preferably 40 mm or less.

b. The spiral height is preferably 3 mm or less. Depending on conditions, preferably, the spiral height is 1.5 mm or less. If the projected portion is excessively low, the grip force is weak and the capsule is raced. Thus, the spiral height with some extent (0.3 mm) or more is necessary and, preferably, the spiral height is 0.3 mm or more and 3 mm or less.

c. Preferably, the spiral cross-section is circular, semicircular, or substantially R-shaped at the projected portion in contact with the body cavity. Based on the examination, the spiral cross-section is also preferably trapezoid.

d. Preferably, the spiral end portion shape (both ends of the thrust generating spiral portion) smoothly rises at the angle of 45° or less along the spiral from the trough to the peak.

e. The number of spiral of the thrust generating spiral portion is preferably two or more and 10 or less, serving as the multi-spiral screw. If the multi-spiral screw is used, the thrust is higher as compared with the single-spiral screw. If the number of spirals is too large, the interval between the peak and the trough is narrow and, on the contrary, the grip force is not large. Under the condition that the pitch is 10 mm or more, the above number is optimum. As a result of examination, the same advantages are obtained by providing the strips along the spiral at the peak of the spiral.

(2) Examination and summary for detecting the magnetic torque (load torque) necessary for stably advancing the body cavity inserting portion in the body cavity such as the small intestine or large intestine:

A. As a result of the examination using the six types of capsules with the spirals having the spiral height of 3 mm or less, the magnetic torque necessary for the advance is 0.2 cNm even in view of the variation and, preferably, it is 0.06 cNm at the lowest level under the optimum condition.

B. Considering the volume of the magnet which can be incorporated in the capsule, the excessively large magnet is not incorporated. The rotating magnetic field of the magnetic field generating means of the extra-body is 150 Oe (oersted), the magnet volume is approximately 830 mm² ($\phi$8 mm×16.5 mm), and the magnetic torque of 1 cNm may be generated.

If the larger magnet is incorporated, the capsule increases in size. If the rotating magnetic field of the extra-body magnetic field generating means is larger than 150 Oe (oersted), the apparatus increases in size. Thus, the arrangement place is restricted and the apparatus increases in price. This results in problems.

C. Based on the foregoing, preferably, the magnetic torque is 0.06 cNm or more and is 1 cNm or less. Further, in consideration of the variation, the magnetic torque is 0.2 cNm or more. In consideration of the safety factor, preferably, the magnetic torque is 0.4 to 0.6 cNm. Further, within the range of the magnetic torque of 1 cNm or less, it is convenient that the operator can arbitrarily set the magnetic torque to a suitable value.

D. By setting the rotating velocity to 5 Hz or less, the capsule is stably rotated. The rotation is converted into the thrust by the spiral portion and the capsule stably advances in the body cavity.

Based on the summary of the examination (examination result), according to the first embodiment, being supplied by the AC current from the AC power supply device 94, the PC 93 shown in FIG. 5 controls the frequency of the rotating magnetic field generated in the triaxial Helmhoz coil 91 to 5 Hz or less. Further, the PC 93 controls the AC power supply device 94 so that the magnetic torque acting on the capsule medical apparatus 1 is 0.06 cNm or more and 1 cNm or less.

Specifically, control program data 93c (stored in a hard disk 93b) for determining the control operation of a CPU 93a in the PC 93 includes control data for controlling the frequency of the rotating magnetic field to be 5 Hz or less that is generated by the AC power supply device 94, and control data for controlling the magnetic torque acting on the capsule medical apparatus 1 to be 0.06 cNm or more and 1 cNm or less.

Hereinbelow, a description is given of the operation of the capsule medical apparatus 1 having the spiral projected portion 37b that is properly set by the above-mentioned measurement data.

Referring to FIG. 1, when the body cavity luminal portion such as a stomach 51 of the patient 2 must to be observed for a long time, the operator allows the patient 2 to swallow the capsule medical apparatus 1 so as to enable the passage of the capsule medical apparatus 1 in the stomach 51.

In this case, the operator previously turns on the switch 27 in the capsule medical apparatus 1 just before the patient 2 swallows the capsule medical apparatus 1. The power supplied by the battery 26a in the battery unit 26 is transmitted to the illuminating device 23, the observing device 24, the digital signal processing circuit 25, and the radio receiving and transmitting circuit 22. Simultaneously, the operator starts (turns on) the magnetic guiding device 5 so that the capsule medical apparatus 1 is magnetically controlled to reach the target portion in the body cavity luminal portion by the rotating magnetic field generated by the magnetic guiding device 5.

As mentioned above, the magnet 36 acts to the rotating magnetic field generated by the magnetic guiding device 5 and then the action of the magnet 36 rotates the capsule main body 6 in the capsule medical apparatus 1. When the capsule main body 6 comes into contact with the inner wall in the body cavity, the capsule medical apparatus 1 advances and returns by converting the friction force between the mucous membrane in the inner wall of the body cavity and the spiral projected portion 37b into large thrust. In accordance with the rotation of the rotating magnetic field, the advancing direction (facing) of the capsule medical apparatus 1 is changed by rotating the capsule main body 6 so that the rotating plane of the magnet 36 matches the rotating plane of the rotating magnetic field.

In this case, the capsule medical apparatus 1 can smoothly reach the target portion in the luminal portion without unnecessary movement such as eccentric motion of the capsule main body 6.

The capsule medical apparatus 1 passes through an esophagus 53 from a mouth 52 by swallowing the capsule medical apparatus 1 by the patient 2 and reaches the stomach 51. In this case, the esophagus 53 has the long diameter of approximately 16 mm and the short diameter of approximately 14 mm and therefore the capsule medical apparatus 1 can easily pass through the esophagus 53 by setting the outer diameter thereof to have the substantially circular cross-section of 14 mm or less. If the outer diameter of the base of the capsule main body 6 is 10 mm, the height of the spiral projected portion 37b is 2 mm or less. If the outer diameter of the base of the capsule main body 6 is 8 mm, the height of the spiral projected portion 37b is 3 mm or less.

When the stomach 51 needs to be observed, the operator inputs the key corresponding to the command for starting the observation from the keyboard 12 in the control device 3. Then, the control signal as the result of the key input is radiated by electric waves via the extra-body antenna 14 in the control device 3 and is transmitted to the capsule medical apparatus 1 side.

The capsule medical apparatus 1 detects a signal for starting the operation based on the signal received by the radio antenna 21, and thus the radio receiving and transmitting circuit 22, the illuminating device 23, the observing device 24, and the digital signal processing circuit 25 are driven.

The illuminating device 23 outputs the illumination light in the field of view of the observing device 24, the optical image within the range of the field of view of the illuminated portion is formed to the image pick-up sensor 32 of the observing device 24 and is photo-electric converted and A/D converted, and the image pick-up signal is outputted. The image pick-up signal is converted into the digital video signal by the video signal processing circuit 34 in the digital signal processing circuit 25. After that, the compression processing circuit 35 compresses the digital video signal, is modulated by the radio receiving and transmitting circuit 22, and is radiated by electric waves from the radio antenna 21.

The electric waves are received by the extra-body antenna 14 in the control device 3, are demodulated by a receiving circuit in the PC main body 11, are converted into the digital signals by the A/D converter in the PC main body 11, and are stored in a memory. Further, the optical image read at the predetermined velocity and picked up by the image pick-up sensor 32 is color-displayed on the monitor 13.

The operator observes the image, thereby observing the stomach 51 in the patient 2. While the observing image, the application of the external magnetic force is easily controlled so as to observe the entire stomach by using the operating means such as the extra-body joystick. The optical image can be recorded to an image recording device (not shown). When the stomach 51 is observed or the capsule medical apparatus 1 is moved from the stomach 51 to the duodenum 54, the smooth operation is possible by the change of the body position of the patient or the pressing operation from outside of the intestine.

After ending the observation of the stomach 51, the capsule medical apparatus 1 is magnetically guided by the rotating magnetic field generated by the magnetic guiding device 5, passes from the stomach 51 through the duodenum 54, the small intestine 55 (refer to FIG. 21), and the large intestine, and is picked up from the anus. In this period, the capsule medical apparatus 1 can observe the inside of the entire digestive tract.

Figure 5B:
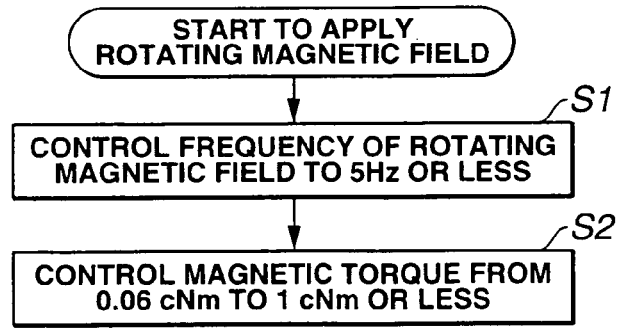
FIG. 5B is a flowchart showing the control operation upon applying the rotating magnetic field.

Upon applying the rotating magnetic field to the capsule medical apparatus 1, referring to FIG. 5B, the CPU 93a in the PC 93 operates in accordance with the program. Then, in step S1, the CPU 93a controls the AC power supply device 94 so that the frequency of the rotating magnetic field is 5 Hz or less. In step S2, the CPU 93a controls the magnetic torque acting to the capsule medical apparatus 1 to be 0.06 cNm or more and 1 cNm or less.

As mentioned above, the capsule medical apparatus 1 according to the first embodiment smoothly reaches the target portion in the luminal portion without unnecessary movement such as the eccentric motion (jiggling) of the capsule main body 6.

The capsule medical apparatus 1 according to the first modification has an improved magnetic guiding efficiency because of the absence of the unnecessary movement. Advantageously, both or one of the magnets in the capsule main body 6 and the one outside of the body is reduced in size.

Referring to FIGS. 21A and 21B, the capsule medical apparatus 1 for spreading the medicine may be used. That is, a capsule medical apparatus 60 has an opening 61a for spreading the medicine which is arranged to the edge of the capsule main body 63 so as to spread the medicine stored in a medicine storage portion 61. Referring to FIGS. 21A and 21B, the capsule medical apparatus 60 in the small intestine 55 is shown.

Further, the capsule medical apparatus 60 for obtaining the body fluid is used. That is, the capsule medical apparatus 60 has, on the rear end thereof, an opening 62a for pouring the body fluid so as to obtain the body fluid in a body fluid storage portion 62 in the capsule main body 63. The opening and closing of the opening 61a for spreading the medicine and the opening 62a for pouring the body fluid are controlled by the communication from the control device 3 described above according to the first embodiment.

Thus, the capsule medical apparatus 60 can release and spread the medicine in the medicine storage portion 61 at the target portion from the opening 61a for spreading the medicine and can obtain the body fluid in the body fluid storage portion 62 from the opening 62a for pouring the body fluid.

The medicine storage portion 61 may store a hemostatic agent for stopping the bleeding and a fluorescer or magnetic fluid that is safe to the living body for determining the bleeding portion from the outside as well as the medicine and can spread them at the target portion.

Further, in the capsule medical apparatus 60, the medicine of the medicine storage portion 61 is mixed in the body fluid taken from the opening 62a for pouring the body fluid and is released and spread from the opening 61a for spreading the medicine. Similarly to the first embodiment, the capsule medical apparatus 60 has the structure in which the center of gravity substantially matches the central axis in the longitudinal direction of the capsule main body 63.

The shape of the spiral projected portion 37b is substantially R-shaped based on the measurement data according to the first embodiment.

As the substantial R-shape in this case, referring to FIG. 22A, the spiral projected portion 37b may be shaped with a semicircular portion 65a and a plane portion 65b. Alternatively, referring to FIG. 22B, the spiral projected portion 37b may be shaped with the semicircular portion 65a. Further, referring to FIG. 22C, the spiral projected portion 37b alternatively may be shaped with an R portion 65c and the plane portion 65b.

According to the first embodiment, referring to FIG. 22D, the spiral projected portion 37b may substantially be trapezoidal-shaped. That is, the spiral projected portion 37b may be shaped with a trapezoidal portion 65d and an R portion 65e having rounded top corners of the trapezoidal portion 65d.

Figure 23A:
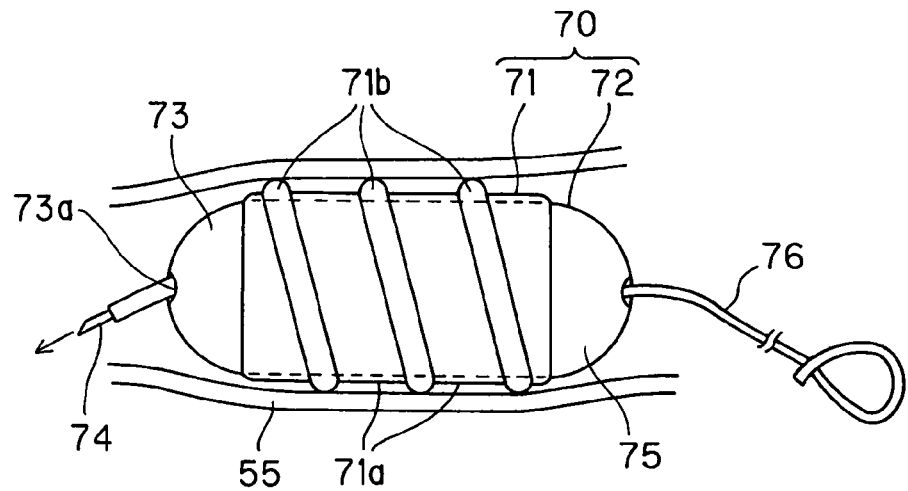

Referring to FIG. 23A, the capsule medical apparatus may have the structure in which an elastic rubber cover, as an exterior member, having a spiral projection is detachably attached to the capsule main body.

Figure 23B:
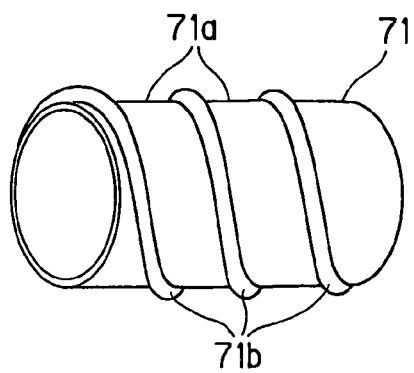

That is, referring to FIGS. 23A and 23B, in a capsule medical apparatus 70, a cylindrical elastic rubber cover 71 having a spiral projection 71b is detachably attached to a capsule main body 72. Thus, the capsule medical apparatus 70 can smoothly advance by the spiral projection 71b of the elastic rubber cover 71, and a fluid such as gas or body fluid flows to the front end and the rear end by a groove 71a between the adjacent projections 71b.

The capsule medical apparatus 70 has a treatment tool storage portion 73 in the capsule main body 72 for the curing and treatment, and has an opening 73a for the treatment tool on the front end side. The opening 73a for the treatment tool is covered by filling a dissolution film containing gelatin digested by the gastric juice or a fatty acid film that is digested by the intestinal juice. In the capsule medical apparatus 70, upon reaching the target portion, the opening 73a for the treatment tool is opened.

The front end side of a treatment tool 74 provided in the treatment tool storage portion 73 is projected or returned from an opening 72a for the treatment tool and the treatment tool 74 can cure or treat the target portion of a body cavity luminal portion 75.

The operation of the treatment tool 74 is controlled under the communication control of the control device 3 as mentioned above according to the first embodiment. The specific operation of the treatment tool 74 may be controlled by operating means such as a joystick or a mouse (not shown) connected to the PC main body 11.

Referring to FIG. 23A, the treatment tool 74 is a needle which can inject a hemostatic agent. In this case, the capsule medical apparatus 70 confirms the bleeding portion by a blood sensor (not shown) or the observing device 24, then, instructs the operation of the treatment tool 74 such as a needle for injecting the hemostatic agent provided in the capsule main body 72 under the communication control of the control device 3, and stops bleeding by spreading ethanol or dry chemical as the hemostatic agent to the bleeding portion.

Further, the capsule medical apparatus 70 has an ultrasonic portion 76 in the capsule main body 72 for examination. The ultrasonic portion 76 has an ultrasonic probe (not shown) which receives and transmits the ultrasonic waves and an ultrasonic control circuit which controls and drives the ultrasonic probe.

In the capsule medical apparatus 70, the ultrasonic probe is watertightly arranged by positioning an acoustic lens portion (not shown) onto the outer surface on the rear end side of the capsule main body 72. On the rear end side of the capsule main body 72, an ultrasonic tomographic image is obtained at the angle of 360°.

Further, in the capsule medical apparatus 70, the obtained data of the ultrasonic tomographic image is modulated by the radio receiving and transmitting circuit 22 similarly to the observed image described according to the first embodiment. The modulated image is radiated by electric waves from the radio antenna 21. Thus, the capsule medical apparatus 70 can perform the diagnosis which determines whether the abnormal portion is present or absent in the depth direction in the deep portion in the body cavity such as a small intestine 55. The capsule medical apparatus 70 can perform the diagnosis of both the surface and the deep portion in the body cavity by arranging both the ultrasonic portion 76 and the observing device 24.

Further, in the capsule medical apparatus 70, the capsule main body 72 has a string 76 with the softness, thickness, and strength to prevent the damage of the luminal portion in the body cavity by a soft resin member for pull-out after the examination from the stomach and small intestine to the mouth or from the large intestine to the anus. The string 76 is softly made so as not to disturb the rotation and advance of the capsule main body 72.

The string 76 is fixed to the outside of the body by coupling the base ends. Similarly to the first embodiment, the capsule medical apparatus 70 has the structure in which the center of gravity of the capsule medical apparatus 70 substantially matches the central axis 38 in the longitudinal direction of the capsule main body 72. A pipe-shaped thin magnet may be put in the elastic rubber cover 71 and the magnet in the capsule main body 72 may not be used. In this case, the normal capsule can easily be modified to a capsule for magnetic guiding.

According to the first embodiment, advantageously, the body cavity inserting portion that is inserted in the body cavity is stably rotated by the external rotating magnetic field. Further, advantageously, the body cavity inserting portion stably and smoothly advances by efficiently converting the rotation into the thrust with the thrust generating unit.

SECOND EMBODIMENT

Next, the second embodiment of the present invention will be described with reference to FIGS. 24 and 25.

Figure 24:
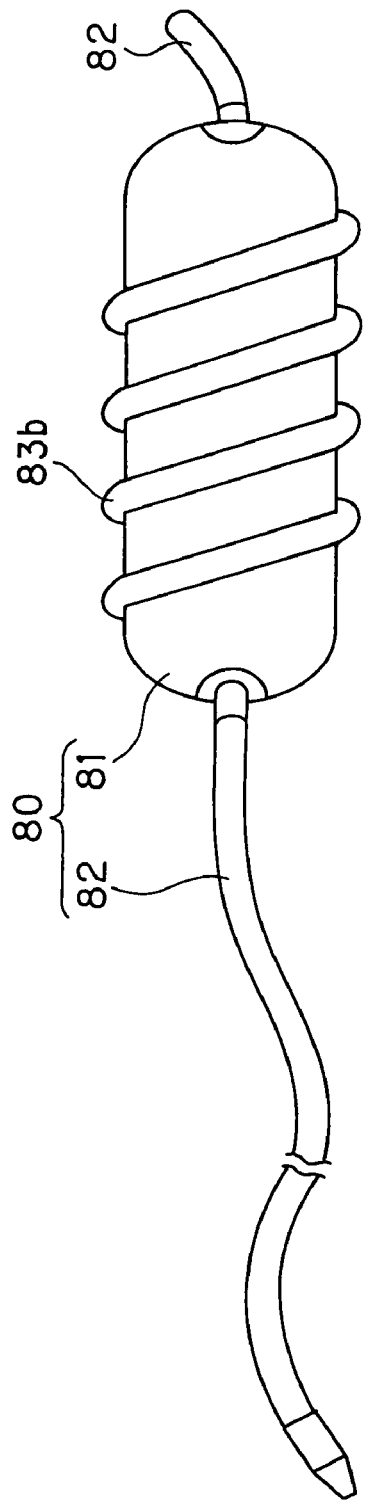
Figure 25:
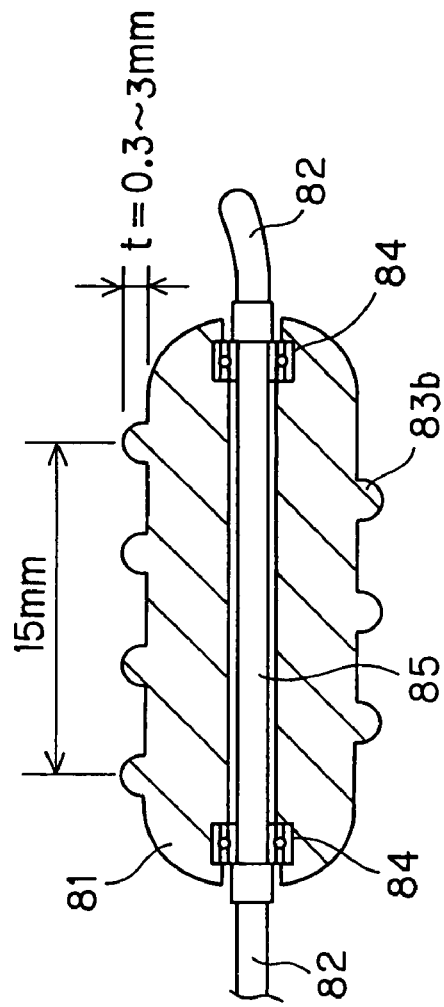

Referring to FIGS. 24 and 25, a capsule medical apparatus 80 according to the second embodiment comprises: a capsule main body 81; and a flexible string portion 82 which is inserted along the central axis of the capsule main body 81. The outer peripheral surface of the capsule main body 81 has a spiral projected portion 83b.

Referring to FIG. 25, the capsule main body 81 has a hollow hole along the central axis. Both ends of a hard rod 85 are rotatably supported to the capsule main body 81 by a bearing 84 such as a ball bearing. The hard rod 85 is inserted into the hollow hole and both ends of the hard rod 85 are connected to the flexible string portion 82.

In this case, one flexible string portion 82 is shortly extended from the capsule main body 81. The other flexible string portion 82 is extended long and the end portion thereof has taper-shaped thin diameter.

According to the second embodiment, referring to FIG. 25, the spiral projected portion 83 has a three-spiral screw having three spiral projected portions 83 at the portion with the length of 15 mm in the capsule main body 81. The capsule main body 81 has a doughnut-shaped magnet (not shown) whose N and S polarities are magnetized in the direction perpendicular to that of the rod 85.

A height t of the spiral projected portion 83 is set to have 0.3 mm to 3 mm.

According to the second embodiment, the capsule main body 81 is inserted from the anus side of the patient as an examinee like the suppository, thereafter, it is magnetically guided in the sequence similar to that according to the first embodiment, and it is rotated, thereby guiding the capsule main body 81 to the deep portion of the large intestine.

The flexible string portion 82 is extended from the capsule main body 81 inserted into the deep portion of the large intestine. The string portion 82 is used as a guiding member and the examining endoscope, an examining device, or the treatment tool is easily inserted into the deep portion of the large intestine, thus to perform the endoscope examination and another examination or treatment.

Upon inserting the capsule main body 81 into the deep portion of the large intestine, the luminal portion of the large intestine is wider than the esophagus or small intestine ($\phi$ of 20 mm or more). Therefore, the capsule main body 81 can smoothly be inserted by shaping the outer diameter of the capsule main body 81 to substantial circular cross-section of 18 mm or less.

Figure 26:
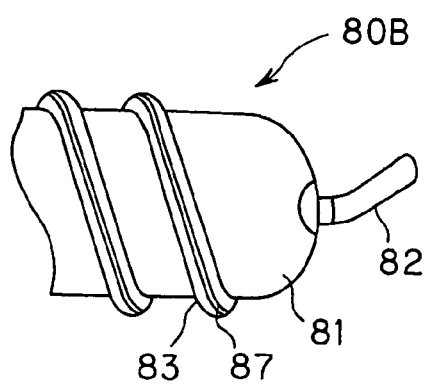
FIGS. 24 to 27 relate to a second embodiment of the present invention.

FIG. 26 shows a part of a capsule medical apparatus 80B according to a first modification. The capsule medical apparatus 80B is obtained by arranging, to the projected portion 83 provided for the capsule main body 81, a groove 87 with a short depth and a short width in the longitudinal direction of the projected portion 83, namely, along the spiral having the projected portion 83, in the capsule medical apparatus 80 shown in FIG. 24.

Figure 27:
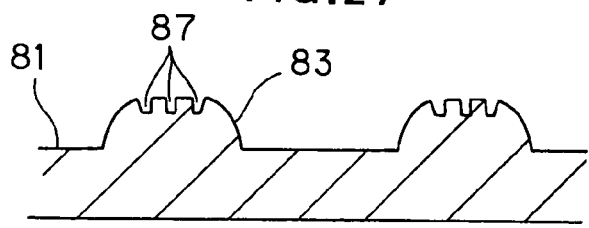

Referring to FIG. 26, one groove 87 is arranged. Further, according to a second modification, referring to FIG. 27, a plurality of grooves 87 may be arranged. That is, e.g., three grooves 87 may be arranged as specifically shown in FIG. 27. According to the first and second modifications, the same operations and advantages as those according to the second embodiment are obtained.

Moreover, according to another embodiment of the present invention, it is possible to arbitrarily change the maximum rotating magnetic field generated by the magnetic field generating means that is externally arranged in the initial state for moving the capsule (static friction state) and in the moving halfway of the capsule (kinetic friction state). Consequently, since the rotation of the capsule over the set value is prevented (the stop of rotation), it is possible to prevent forcible passage at the narrow portion in the body cavity when the operator does not intend it. Therefore, the capsule can move from the stop portion thereof under the management of the operator.

In the above description, the rotation driving means for rotating the capsule medical apparatus (hereinafter, referred to the capsule) is the magnetic field generated by the external magnetic field generating means. However, the present invention is not limited to this and can apply another rotation driving means.

For example, as the means for rotating the capsule, a dielectric (polarized like a condenser) may be arranged to the capsule. The electric field is applied to the dielectric with rotating from the outside, thereby rotating the capsule.

Further, in the case of a medical apparatus with a shaft instead of the capsule medical apparatus, a flexible shaft with the close coiling used for an ultrasonic probe is rotatably arranged to the shaft, a motor on the hand side is rotated, rotating a spiral projected portion for generating thrust, thereby advancing the capsule.

The body cavity inserting portion is not limited to the above-mentioned capsule medical apparatus. For example, like the capsule medical apparatus 80 shown in FIG. 24, the spiral projected portion for generating thrust having the magnet is rotatably fixed near a string member such as a flexible guiding wire, string, or tube or near the edge of a flexible stick portion of the normal endoscope, the external magnetic field generating means or another rotating means generates the rotating magnetic field, the spiral projected portion for generating thrust receives the magnetic field and generates thrust simultaneously to the rotation, and thus the string member or flexible stick portion is conveyed to the target portion in the deep portion in the body cavity. Further, necessary one of the above structures is properly selected and is combined to embody the body cavity inserting portion.

In the above description, the spiral projected portion for generating thrust is used. However, according to the present invention, the thrust generating unit may have the projected portion that is spiral-shaped. The projected portion in this case may spirally be in contact with the inner wall of the body cavity when the projected portion is inserted in the body cavity.

Therefore, the projected portion may not spirally and continuously be formed. For example, the projected portion may partly be notched. Alternatively, a plurality of the projected portions may be arranged along the spiral portion.

INDUSTRIAL APPLICABILITY

As mentioned above, the capsule medical apparatus according to the present invention has, onto the outer peripheral surface of the inserting portion, the spiral projected portion with the proper pitch and height. Therefore, the capsule medical apparatus rotates by applying the rotating magnetic field, and stably and smoothly advances in the body cavity by efficiently converting the rotation into the thrust.

The invention claimed is:

1. A medical apparatus, comprising:
a body cavity inserting portion which is inserted into a body and which has a thrust-generating spiral projected portion in contact with a body cavity; and
rotating device for rotating the thrust-generating spiral projected portion, wherein
the rotating device includes:
a magnetic field generating device arranged outside the body for generating a rotating magnetic filed; and
a magnet arranged inside the body cavity inserting portion and driven to rotate by the rotating magnetic field;
the thrust-generating spiral projected portion is set to have a shape with a projection height from not less than 0.3 mm to not more than 3 mm; and
the rotating magnetic field is set to rotate at a rotating speed of not more than 5 Hz.

2. The medical apparatus according to claim 1, wherein the thrust-generating spiral projected portion is formed in a multi-spiral screw shape having not less than 2 spirals.

3. The medical apparatus according to claim 1, wherein the thrust-generating spiral projected portion has a cross sectional shape of at least one of a circle, a semicircle and a generally R shape.

4. The medical apparatus according to claim 1, wherein the thrust-generating spiral projected portion is non-continuously formed.

5. The medical apparatus according to claim 1, wherein the body cavity inserting portion is a capsule medical apparatus.

6. The medical apparatus according to claim 1, wherein:
the body cavity inserting portion includes a flexible stick portion; and
the thrust-generating spiral projected portion is supported rotatably with respect to the flexible stick portion.

7. The medical apparatus according to claim 1, wherein:
the thrust-generating spiral projected portion is formed in a multi-spiral screw shape having not more than 10 spirals.

8. The medical apparatus according to claim 1, wherein:
a torque generated by the rotating device is set so as not to surpass a set value.

9. The medical apparatus according to claim 8, wherein a set value for the torque generated by therotating device is configured to be arbitrarily settable.

10. The medical apparatus according to claim 8, wherein the set value is set to from not less than 0.06 cNm to not more than 1 cNm.

11. The medical apparatus according to claim 10, wherein the body cavity inserting portion is a capsule medical apparatus.

12. The medical apparatus according to claim 1, wherein:
at least one of a rising angle and a falling angle at an end portion of the trust-generating spiral projected portion is smoothly formed at an angle not more than 45 degrees.

13. The medical apparatus according to claim 1, wherein:
the thrust-generating spiral projected portion has an outer diameter of not more than 18 mm.

14. The medical apparatus according to claim 1, wherein:
the thrust-generating spiral projected portion has at least one groove formed along the spiral of the thrust-generating spiral projected portion, the groove having a depth smaller than a height of the thrust-generating spiral projected portion.

15. The medical apparatus according to claim 1, wherein:
the thrust-generating spiral projected portion is detachably attached to the body cavity inserting portion.

16. The medical apparatus according to claim 15, wherein the thrust-generating spiral projected portion is formed of elastic rubber.

17. The medical apparatus according to claim 1, wherein:
the thrust-generating spiral projected portion has a generally trapezoidal cross sectional shape.

18. The medical apparatus according to claim 1, wherein:
the thrust-generating spiral projected portion has a spiral pitch which is set to not less than 10 mm.

19. The medical apparatus according to claim 1, wherein:
a center of gravity of the body cavity inserting portion substantially matches a longitudinal central axis of the body cavity inserting portion.

20. the medical apparatus according to claim 1, wherein the thrust-generating spiral projected portion is set to have a shape with a projection height from not less than 0.3 mm to not more than 2 mm.

* * * * *